US012194308B2

United States Patent
Yakobson et al.

(10) Patent No.: US 12,194,308 B2
(45) Date of Patent: Jan. 14, 2025

(54) EXTERNAL ELECTRONIC PATCH FOR ACCELERATING BONE HEALING OR REGENERATION AFTER TRAUMA

(71) Applicant: Pulsar Medtech Ltd., Bnei-Brak (IL)

(72) Inventors: Elad Yakobson, Tel-Aviv (IL); Shlomo Barak, Tel-Aviv (IL)

(73) Assignee: Pulsar Medtech Ltd., Bnei-Brak (IL)

( * ) Notice: Subject to any disclaimer, the term of this patent is extended or adjusted under 35 U.S.C. 154(b) by 686 days.

(21) Appl. No.: 16/963,231

(22) PCT Filed: Jan. 18, 2019

(86) PCT No.: PCT/IL2019/050074
§ 371 (c)(1),
(2) Date: Jul. 19, 2020

(87) PCT Pub. No.: WO2019/142196
PCT Pub. Date: Jul. 25, 2019

(65) Prior Publication Data
US 2021/0361965 A1      Nov. 25, 2021

Related U.S. Application Data

(60) Provisional application No. 62/618,685, filed on Jan. 18, 2018.

(51) Int. Cl.
*A61N 2/00*      (2006.01)
*A61N 2/02*      (2006.01)
(52) U.S. Cl.
CPC ............ *A61N 2/004* (2013.01); *A61N 2/02* (2013.01)

(58) Field of Classification Search
CPC ........ A61N 2/004; A61N 2/02; A61N 1/0484; A61N 1/40; A61N 1/0468
(Continued)

(56) References Cited

U.S. PATENT DOCUMENTS

| 4,574,809 A | 3/1986 | Talish et al. |
| 4,942,884 A * | 7/1990 | Ichinomiya ............. A61N 5/04 607/98 |

(Continued)

FOREIGN PATENT DOCUMENTS

| AU | 2015207951 | 8/2015 |
| AU | 2015268576 | 12/2015 |

(Continued)

OTHER PUBLICATIONS

Notice of Reason(s) for Rejection Dated Jan. 31, 2023 From the Japan Patent Office Re. Application No. 2020-560643. (4 pages).
(Continued)

*Primary Examiner* — Sunita Reddy

(57) ABSTRACT

An electronic patch, for stimulating tissue healing at a target site, is flexible enough to generally conform to a body surface adjacent to the target site, and includes: a battery or an arrangement of multiple batteries less than 5 mm thick; a capacitor connected directly with a coil in series; and pulse generating circuitry, powered by the battery or batteries. The circuitry repeatedly changes the voltage across the capacitor and coil, to produce pulses of current in the coil. The current produces a pulsed electromagnetic field at the target site for stimulating tissue healing, most of the electromagnetic field energy of each pulse being converted into electrostatic energy of the capacitor at the end of the pulse and back into electromagnetic field energy of the next pulse.

23 Claims, 17 Drawing Sheets

(58) Field of Classification Search
USPC .................................................... 600/9–15
See application file for complete search history.

(56) References Cited

U.S. PATENT DOCUMENTS

| | | | |
|---|---|---|---|
| 4,998,532 | A | 3/1991 | Griffith |
| 5,014,699 | A | 5/1991 | Pollack et al. |
| 5,413,596 | A | 5/1995 | Kronberg |
| 5,591,212 | A | 1/1997 | Keimel |
| 5,792,209 | A * | 8/1998 | Varner ................... A61N 1/326 607/51 |
| 5,951,459 | A | 9/1999 | Blackwell |
| 6,132,362 | A | 10/2000 | Tepper et al. |
| 6,179,772 | B1 | 1/2001 | Blackwell |
| 6,261,221 | B1 | 7/2001 | Tepper et al. |
| 6,792,313 | B2 | 9/2004 | Nachum |
| 7,043,308 | B2 | 5/2006 | Cohen |
| 2001/0003799 | A1 | 6/2001 | Bovcja |
| 2003/0032852 | A1 | 2/2003 | Perreault et al. |
| 2004/0039433 | A1 * | 2/2004 | Wodnicki ................. A61N 1/40 607/115 |
| 2004/0267333 | A1 * | 12/2004 | Kronberg ........... A61N 1/36021 607/72 |
| 2006/0212077 | A1 | 9/2006 | Pilla et al. |
| 2010/0210893 | A1 * | 8/2010 | Pilla ....................... A61N 2/008 47/1.01 R |
| 2011/0004261 | A1 * | 1/2011 | Sham ....................... A61F 7/034 607/3 |
| 2012/0253098 | A1 | 10/2012 | George et al. |
| 2014/0249355 | A1 * | 9/2014 | Martinez ................. A61N 2/004 600/14 |
| 2014/0303425 | A1 * | 10/2014 | Pilla ....................... A61B 6/037 600/15 |
| 2014/0371802 | A1 | 12/2014 | Mashiach et al. |
| 2015/0094521 | A1 | 4/2015 | Neuman et al. |
| 2016/0067517 | A1 * | 3/2016 | Burnett .................. A61N 2/008 600/14 |
| 2017/0021172 | A1 | 1/2017 | Perez et al. |
| 2018/0015295 | A1 | 1/2018 | Neuman et al. |
| 2020/0206523 | A1 * | 7/2020 | Kirk ................... A61N 1/36014 |

FOREIGN PATENT DOCUMENTS

| | | |
|---|---|---|
| CN | 1115256 | 1/1996 |
| CN | 102076245 | 5/2011 |
| CN | 203898943 | 10/2014 |
| CN | 107148296 | 9/2017 |
| EP | 1059965 | 12/2000 |
| JP | H11-511661 | 10/1999 |
| KR | 10-2016-0131716 | 11/2016 |
| TW | M475962 U | 4/2014 |
| WO | WO 99/44685 | 9/1999 |
| WO | WO 2019/142196 | 7/2019 |

OTHER PUBLICATIONS

Translation Dated Feb. 21, 2023 of Notice of Reason(s) for Rejection Dated Jan. 31, 2023 From the Japan Patent Office Re. Application No. 2020-560643.(5 pages).
Factor et al. "The Effects of Novel Pulsed Electromagnetic Field Therapy Device on Acute Distal Radius Fractures: A Prospective, Double-Blind, Sham-Controlled, Randomized Pilot Study", Journal of Clinical Medicine, 12(5): 1866-1-1866-12, Published Online Feb. 27, 2023.
Communication Pursuant to Article 94(3) EPC Dated Jul. 15, 2022 From the European Patent Office Re. Application No. 19703201.4. (7 Pages).
International Preliminary Report on Patentability Dated Jul. 30, 2020 From the International Bureau of WIPO Re. Application No. PCT/IL2019/050074. (10 Pages).
International Search Report and the Written Opinion Dated Mar. 21, 2019 From the International Searching Authority Re. Application No. PCT/IL2019/050074. (18 Pages).
Assiotis et al. "Pulsed Electromagnetic Fields for the Treatment of Tibial Delayed Unions and Nonunions. A Prospective Clinical Study and Review of the Literature", Journal of Orthopaedic Surgery and Research, 7(24): 45-59, Published Online Jun. 8, 2012.
Barak et al. "A New Device for Improving Dental Implants Anchorage: A Histological and Micro-Computed Tomography Study in the Rabbit", Clinical Oral Implants Research, 27(8): 935-942, Published Online Aug. 6, 2015.
Barak et al. "Antimicrobial Effects of Pulsed Electromagnetic Field: In-Vitro Polymicrobial Periodontal Subgingival Biofilm Model", Journal of Clinical Periodontology, 45(Suppl.19): 100, # PD162, Published Online Jun. 20, 2018.
Barak et al. "Miniaturized Electromagnetic Device Abutment Improves Stability of the Dental Implants", The Journal of Craniofacial Surgery, 30(4): 1055-1057, Jun. 2019.
Chalidis et al. "Stimulation of Bone Formation and Fracture Healing With Pulsed Electromagnetic Fields: Biologic Responses and Clinical Implications", International Journal of Immunopathology and Pharmacology, 24(1/Suppl.2): 17-20, Jan.-Mar. 2011.
Cook et al. "Healing in the New Millennium: Bone Stimulators. An Overview of Where We've Been and Where We May Be Heading", Clinics in Podiatric Medicine & Surgery, 32(1): 45-59, Jan. 2015.
Ferroni et al. "Pulsed Electromagnetic Fields Increase Osteogenetic Commitment of MSCs Via the mTOR Pathway in TNF-Alpha Mediated Inflammatory Conditions: An In-Vitro Study", Scientific Reports, 8: 5108-1-5108-13, Published Online Mar. 23, 2018.
Galli et al. "The Use of Pulsed Electromagnetic Fields to Promote Bone Responses to Biomaterials In Vitro and In Vivo", International Journal of Biomaterials, 2018(Art.ID 8935750): 1-15, Published Online Sep. 3, 2018.
Hannemann et al. "The Effects of Low-Intensity Pulsed Ultrasound and Pulsed Electromagnetic Fields Bone Growth Stimulation in Acute Fractures: A Systematic Review and Meta-Analysis of Randomized Controlled Trials", Archives of Orthopaedic and Trauma Surgery, 134(8): 1093-1106, Published Online Jun. 4, 2014.
Lazovic et al. "Pulsed Electromagnetic Field During Cast Immobilization in Postmenopausal Women With Colles' Fracture", Srpski Arhiv za Celokupno Lekarstvo, 140(9-10): 619-624, Sep.-Oct. 2012.
Nayak et al. "Effect of the Pulsed Electromagnetic Field (PEMF) on Dental Implants Stability: A Randomized Controlled Clinical Trial", Materials, 13(7): 1667-1-1667-9, Published Online Apr. 3, 2020.
Shi et al. "Early Application of Pulsed Electromagnetic Field in the Treatment of Postoperative Delayed Union of Long-Bone Fractures: A Prospective Randomized Controlled Study", BMC Musculoskeletal Disorders, 14(1): 35-1-35-7, Dec. 2013.
Requisition Dated Oct. 20, 2023 From the Innovation, Science and Economic Development Canada, Canadian Intellectual Property Office Re. Application No. 3,088,298. (4 Pages).
Supplementary European Search Report and the European Search Opinion Dated Nov. 17, 2023 From the European Patent Office Re. Application No. 23193941.4. (8 Pages).
English Summary and Translation Dated Aug. 30, 2023 of Notification of Office Action Dated Aug. 21, 2023 From the State Intellectual Property Office of the People's Republic of China Re. Application No. 201980017743.0. (7 pages).
Notice of Reason(s) for Rejection Dated Aug. 8, 2023 From the Japan Patent Office Re. Application No. 2020-560643. (2 pages).
Notification of Office Action and Search Report Dated Aug. 21, 2023 From the State Intellectual Property Office of the People's Republic of China Re. Application No. 201980017743.0. (9 Pages).
Requisition Dated Aug. 7, 2024 From the Innovation, Science and Economic Development Canada, Canadian Intellectual Property Office Re. Application No. 3,088,298. (4 Pages).

* cited by examiner

Top view (Without silicone topping)

Cross section view block diagram

EXTERNAL ELECTRONIC PATCH FOR ACCELERATING BONE HEALING OR REGENERATION AFTER TRAUMA

RELATED APPLICATION/S

This application is a National Phase of PCT Patent Application No. PCT/IL2019/050074 having International filing date of Jan. 18, 2019, which claims the benefit of priority under 35 USC § 119 (e) of U.S. Provisional Patent Application No. 62/618,685, filed on Jan. 18, 2018. The contents of the above applications are all incorporated by reference as if fully set forth herein in their entirety.

FIELD AND BACKGROUND OF THE INVENTION

The present invention, in some embodiments thereof, relates to the field of devices for enhanced tissue healing. More particularly, the invention relates to an electronic patch externally applied to an injured limb to promote bone healing and regeneration.

Fractures are very common types of body trauma. In the United States, approximately 5.6 million fractures occur each year. In England, the fracture incidence for all age groups is 3.6% every year. Moreover, it is suggested that >33% of people will experience a fracture in their life time. Bone fractures may be treated either conservatively or surgically. Surgical treatment comprises different methods of fixing the broken bones, such as internally-placed nails, or pins incorporated into an external frame (external fixation). Non-surgical or conservative treatment usually involves different types of plaster casts. A notable proportion of fractures are treated conservatively with cast immobilization.

Meanwhile, 5% to 10% of these fractures show delayed healing or nonunion. The delay unions or mal/non-unions often require further intervention and may cause serious complications, such as pain and functional limitations. Invasive and expensive re-operation is usually necessary to promote bone healing. To reduce the substantial risk of disability and the socioeconomic costs, the development of a method for accelerating fracture healing is becoming more and more important. In some cases, a surgical intervention is also required. A surgical procedure for internally fixating fractured bones with biocompatible and durable implants has widespread acceptance, while reducing the incidence of nonunion and malunion of broken bones. However, bones internally fixated with such implants are susceptible to muscle and nerve damage due to the presence of the implants and have a prolonged recovery time.

U.S. Pat. No. 6,261,221 to Tepper et al describes a PEMF (pulsed electromagnetic field) therapy system that uses a single-coil PEMF transducer for generating PEMF stimulation signals. The coil has a "bi-phasic" operation, such that current flows through it in two directions. A drive circuit recovers the flyback energy from the transducer coil and dumps voltage to an energy recovery capacitance circuit. The transducer is thereby energized and de-energized to provide the electromagnetic field. The single coil transducer may be fabricated on a flexible substrate and the wiring may be formed with printed circuit techniques. The same concepts may be applied to series connected coils.

U.S. Patent Application Publication No. US2018/0015295-A1, "Bone Enhancement Device and Method," to Moshe Neumann, Roni Daffan, and Joseph Shechter, published Jan. 18, 2018, describes an energy saving circuit configured for electro-magnetic orthopedic therapy, the circuit comprising:
a coil arranged to produce an orthopedic therapeutic electro-magnetic field;
a capacitor in series with the coil;
one or more switches in series with the capacitor; and
a controller to:
control the switches to maintain the capacitor at a first voltage value during a non-pulse phase, wherein no electro-magnetic field is produced;
control the switches to charge the capacitor to a second voltage value, the second voltage value equal to the first voltage value, the second voltage value having a charge opposite to the first voltage value; and
control the switches to further charge the capacitor from the second voltage value back to the first voltage value, the further charging occurring over a time period of a pulse phase, wherein the charging and the further charging the capacitor comprises passing a current through the coil to produce the electro-magnetic field, the current related to a voltage drop across the coil of about two times the first voltage.

U.S. Patent Application Publication No. 2006/212077 to Pilla et al describes, in FIG. 2, "Waveforms configured by the miniature control circuit 201 . . . directed to a generating device 203 such as electrical coils via connector 202. The generating device 203 delivers a pulsing magnetic field that can be used to provide treatment to a target pathway structure such as tissue."

U.S. Pat. No. 4,574,809 to Talish et al, Portable Non-Invasive Electromagnetic Therapy Equipment," describes "a cast-embeddable coil structure which includes a single connector fitting, designed for exposure externally of a completed cast and for removable mounting and electrical connection to a self-contained light-weight rechargeable portable signal generator unit. The signal-generator unit is mounted to the cast only for periods of therapeutic treatment, and it is removably mounted to a less-portable charging unit in intervals between periods of therapeutic treatment."

U.S. Pat. No. 4,998,532 to Griffith describes, "A portable non-invasive apparatus for electro-therapeutic stimulation of tissue and bone healing readily worn and carried by a patient." He states that "a coil-type transducer is most preferred for treating deep bone fractures," and compares the power needed using "Helmholtz paired coils, simple coil, simple coil oblique to the fracture or solenoid."

The following papers describe controlled studies of the effectiveness of PEMF for treating bone fractures: Hong-fei Shi et al, "Early application of pulsed electromagnetic field in the treatment of postoperative delayed union of long-bone fractures: a prospective randomized controlled study," *BMC Musculoskeletal Disorders* 2013, 14:35; Milica Lazovic et al, "Pulsed Electromagnetic Field During Cast Immobilization in Postmenopausal Women with Colles' Fracture," *Srp Arh Celok Lek.* 2012 September-October:140(9-10):619-624; and Aggelos Assiotis et al, "Pulsed electromagnetic fields for the treatment of tibial delayed unions and non-unions. A prospective clinical study and review of the literature," *Journal of Orthopaedic Surgery and Research* 2012, 7:24.

The following papers provide reviews of the literature on PEMF treatment of bone fractures: Jeremy J. Cook et al, "Healing in the New Millenium: Bone Stimulators," *Clin Podiatr Med Surg* 32 (2015) 45-59; B. Chalidis et al, "Stimulation of Bone Formation and Fracture Healing with Pulsed Electromagnetic Fields: Biologic Responses and Clinical Implications," *International Journal of Immunopathology and Pharmacology* 24, no. 1 (S2), 17-20 (2011); and Carlo Galli et al, "The Use of Pulsed Electromagnetic Fields to Promote Bone Responses to Biomaterials *In Vitro and In Vivo.*" *International Journal of Biomaterials* 2018, Article ID 8935750, 15 pages.

Additional background art includes U.S. Pat. No. 5,413,596 to Kronberg, U.S. Pat. No. 6,792,313 to Nachum, U.S. Pat. No. 7,043,308 to Cohen, China Published Patent Application CN203898943 to Sun Zechuan (English abstract), South Korea Published Patent Application No. KR2016/0131716 to Ku Jeong Hun et al (English abstract).

SUMMARY OF THE INVENTION

An aspect of some embodiments of the invention concerns an electronic patch that produces pulsed electromagnetic fields to promote tissue healing, and that optionally uses a resonant energy-saving circuit to recycle field energy from one pulse to the next, potentially allowing a smaller and thinner battery to be used, allowing the patch to be thin and flexible. There is thus provided, according to an exemplary embodiment of the invention, an electronic patch for stimulating tissue healing at a target site, flexible enough to generally conform to a body surface adjacent to the target site, comprising:
  a) a battery or an arrangement of multiple batteries less than 5 mm thick;
  b) a capacitor in series with a coil;
  c) pulse generating circuitry, powered by the battery or batteries, which repeatedly changes the voltage across the capacitor and coil, to produce pulses of current in the coil, the current producing an electromagnetic field at the target site for stimulating tissue healing during the pulse period, most of the electromagnetic field energy coming from the capacitor at the beginning of the pulse period and returning to the capacitor at the end of the pulse period.

Optionally the pulse generator is configured to produce one or more further pulse periods during which the coil produces the electromagnetic field at the target site, with at least some of the pulse periods alternating with non-pulse periods in which, substantially no electromagnetic field is produced at the target site.

Optionally, the current in the coil during the non-pulse periods is no greater than 10 μA.

Optionally, the pulse generator is configured to produce pulses at intervals such that a duty cycle, defined as a ratio of the pulse periods to the total time, is less than 10%.

Optionally, the duty cycle is less than 1%.

Optionally, the non-pulse periods are between 0.02 and 0.5 seconds.

Optionally, more than 90% of the electromagnetic field energy comes from the capacitor at the beginning of the pulse period and returns to the capacitor at the end of the pulse period.

Optionally, any rigid component of the patch is no wider than 25 mm in a direction that the patch is flexible in, and any two rigid components of the patch, arranged in a direction that the patch is flexible in, are separated by at least 1.5 mm.

Optionally, the patch comprises flexible electronic components.

Optionally, the battery, or the batteries collectively, have a capacity less than 2000 mA-hrs.

Optionally the battery, or the batteries collectively, have a capacity of less than 250 mA-hrs.

Optionally, the patch is less than 10 mm thick.

Optionally, the pulse period is between 5 microseconds and 50 microseconds, in steady state operation.

Optionally, the peak current in the coil is between 25 mA and 3 A.

Alternatively, the peak current in the coil is between 0.1 mA and 25 mA.

Optionally, the magnetic field at the target site is between 0.05 and 0.5 mT.

Optionally, the patch comprises a substrate of bio-compatible silicone, which provides the patch with flexibility.

Optionally, the total voltage across the battery or the arrangement of batteries is between 1.5 and 6 volts.

Optionally, the electronic patch comprises a one-way or two-way wireless communications link.

Optionally, the electronic patch comprises a timer that automatically deactivates the patch by disconnecting the battery or batteries, and reactivates the patch by reconnecting the battery or batteries, at preset times.

Optionally, the electronic patch is water resistant for 24 hours continuous exposure to water.

Optionally, the electronic patch is water resistant for 100 half-hour exposures to water, or for both 24 hours continuous exposure to water and 100 half-hour exposures to water.

Optionally, the coil is oval or race course shaped when the patch is flat.

Optionally, the patch is for use on a sternum, and the coil has a major diameter and a minor diameter both between 8 and 12 cm, and less than 10 mm thick.

Alternatively, the patch is for use on a skull, and the coil has a major diameter and a minor diameter both between 6 and 10 cm, and less than 10 mm thick.

Alternatively, the patch is for use on a rib, and the coil has a major diameter between 8 and 12 cm, a minor diameter both between 4 and 6 cm, and less than 10 mm thick.

Alternatively, the patch is for use on a spine, and the coil has a major diameter between 6 and 10 cm, a minor diameter both between 4 and 6 cm, and less than 10 mm thick.

There is further provided, according to an exemplary embodiment of the invention, a method of treating a fractured bone site in a body part, comprising:
  a) applying the electronic patch to an outer surface of the body part;
  b) setting the body part in a cast that covers the electronic patch; and
  c) while the electronic patch is covered by the cast, using the controller to produce an electromagnetic field at the fractured bone site suitable for stimulating osteogenesis, during multiple pulse periods, with most of the electromagnetic field energy coming from the capacitor at the beginning of each pulse period and returning to the capacitor at the end of each pulse period.

Optionally, the electronic patch comprises a pressure sensor with a communications link to the outside of the cast, and the method also comprises measuring a pressure of the cast against the body part at different times during the treatment of the bone site and communicating the measured pressure over the communications link.

Optionally, if the pressure measurement shows a rise in pressure indicative of an increase in swelling of the body part, or if the pressure measurement shows a fall in pressure indicative of the cast being too loose, the method comprises communicating that information to medical personnel.

Optionally, the electronic patch comprises a blood oxygen sensor with a communications link to the outside of the cast, and the method also comprises measuring the blood oxygen level in the skin of the body part at different times during the treatment of the bone site and communicating the measured blood oxygen level over the communications link.

Optionally, if the blood oxygen level shows a drop over time indicative of the cast being too tight, the method comprises communicating that information to medical personnel.

Optionally, the patch is for use on a cylindrical body part, sized to wrap at least part way around the cylindrical body part, with a first portion of the patch, comprising the coil, on one side, and a second portion of the patch comprising another coil, on another side, with the other coil also contributing to the electromagnetic field at the bone site when current flows in it, and with the pulse generator configured to transfer most of the electromagnetic field energy of both coils from the same and/or a different capacitor at the beginning of the pulse period and to return most of the electromagnetic field energy of both coils to said capacitor or capacitors at the end of the pulse period.

Optionally, the patch is for use on a hand, and the coils have major and minor diameter both between 3 cm and 8 cm, and thickness less than 5 mm.

Optionally, the patch is for use on a leg, and the coils have major diameter between 32 and 50 cm, minor diameter between 16 cm and 25 cm, and thickness less than 5 mm.

Optionally, the patch is for use on a pelvis, and the coils have major diameter between 32 and 50 cm, minor diameter between 12 cm and 20 cm, and thickness less than 5 mm.

There is further provided, according to an exemplary embodiment of the invention, an electronic patch for stimulating tissue healing at a target site inside a cylindrical body part, suitably sized to wrap at least partly around the body part, with a first part of the patch on one side of the body part, and a second part of the patch on another side of the body part, the patch comprising:
   a) a battery or an arrangement of multiple batteries;
   b) a first coil located in the first part of the patch, and a second coil in the second part of the patch; and
   c) a controller, powered by the battery or batteries, configured in a first mode of operation to pass a current through the first coil, producing an electromagnetic field at the target site for stimulating tissue healing, and to measure an electromotive force (emf) voltage induced in the second coil by the current passing through the first coil.

Optionally, the patch is flexible enough to generally conform to the body part when it is wrapped around the body part.

Optionally, the patch has a second mode of operation wherein the controller is configured to pass current through both coils, the two coils producing an electromagnetic field at the target site for stimulating tissue healing.

There is further provided, according to an exemplary embodiment of the invention, a method of adjusting an intensity of the electromagnetic field at a target site in a cylindrical body part to a specified value, comprising:
   a) wrapping the electronic patch at least partly around the body part;
   b) operating the electronic patch in the first mode of operation, measuring the emf voltage induced in the second coil by a known current in the first coil;
   c) using the measured emf to estimate a required level of current for the first coil, or to estimate a required level of current for the first and second coils, to produce the specified level of electromagnetic field at the target site; and
   d) passing the required level of current for the first coil in the first coil, or passing the required level of current for the first and second coils in the first and second coils, producing the specified level of electromagnetic field at the target site.

There is further provided, according to an exemplary embodiment of the invention, a method of monitoring a target site in a cylindrical body part during a course of treatment with electromagnetic fields to stimulate tissue healing, the method comprising:
   a) wrapping the electronic patch at least partly around the body part, with the two coils on different sides of the body part;
   b) passing current through the first coil, or through the first and second coils, to treat the target site;
   c) operating the electronic patch in the first mode of operation at different times during the course of treatment, measuring the emf voltage in the second coil induced by a known current in the first coil at each of the times; and
   d) if the induced emf voltage in the second coil for a given current in the first coil is decreasing over time at a rate and to an extent that indicates a medically significant increase in swelling of the body part, notifying medical personnel of the increase in swelling.

There is further provided, according to an exemplary embodiment of the invention, a method of monitoring a target site in a cylindrical body part during a course of treatment with electromagnetic fields to stimulate tissue healing, the method comprising:
   a) wrapping the electronic patch at least part way around the body part, with the two coils on different sides;
   b) setting a cast over the electronic patch;
   c) passing current through the first coil, or through the first and second coils, to treat the target site;
   d) operating the electronic patch in the first mode of operation at different times during the course of treatment, measuring the emf voltage in the second coil induced by a known current in the first coil at each of the times; and
   e) notifying medical personnel if the emf voltage induced in the second coil by a given current in the first coil decreases at a rate and to an extent that is indicative of a medically significant increase in swelling of the body part, or increases at a rate and to an extent indicative of the cast becoming too loose.

There is further provided, according to an exemplary embodiment of the invention, a method of calibrating the electronic patch, comprising:
   a) arranging the patch so that the first coil and the second coil are at a specified relative position and orientation to each other;
   b) passing a specified current through the first coil; and
   c) measuring the emf induced in the second coil by the current in the first coil.

There is further provided, according to an exemplary embodiment of the invention, a method of treating a fractured bone site in a body part, comprising:
   a) applying an electronic patch, comprising an electronics package, a battery and a coil in a flexible substrate, to an outer surface of the body part;
   b) setting the body part in a cast that covers the entire electronic patch; and
   c) while the electronic patch is covered by the cast, using the patch to produce an electromagnetic field at the fractured bone site suitable for stimulating osteogenesis.

There is further provided, according to an exemplary embodiment of the invention, an electronic patch, flexible enough and of suitable size to wrap at least partly around a body part while generally conforming to the surface of the body part, comprising two flexible coils, located on different sides of the body part when the patch is wrapped around the body part, that produce pulsed electromagnetic fields at a target site inside the body part, to promote tissue healing.

There is further provided, according to an exemplary embodiment of the invention, a flat flexible electronic patch with horizontal and vertical axes, comprising two coils arranged horizontally, each with a central hole at least 20 mm across, the patch configured to wrap horizontally at least part way around a cylindrical axis of a cylindrical body part and for the coils to generate pulsed electromagnetic fields for healing tissue at a target site inside the cylindrical body part, the patch also comprising one or more electronic elements that are substantially opaque to medical x-rays, the electronic elements all being mounted on the patch at positions displaced in a vertical direction by at least 10 mm from the centers of the holes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 14:
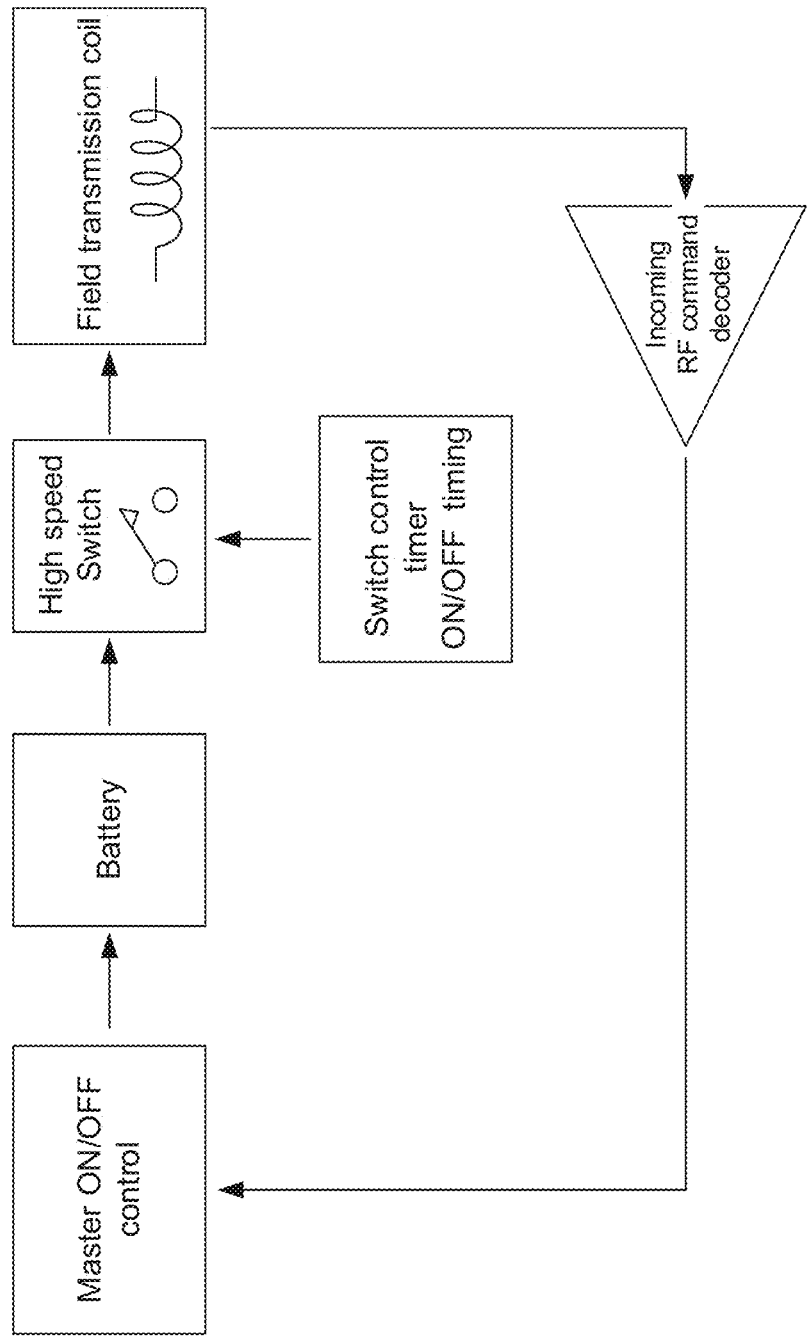
Figure 15:
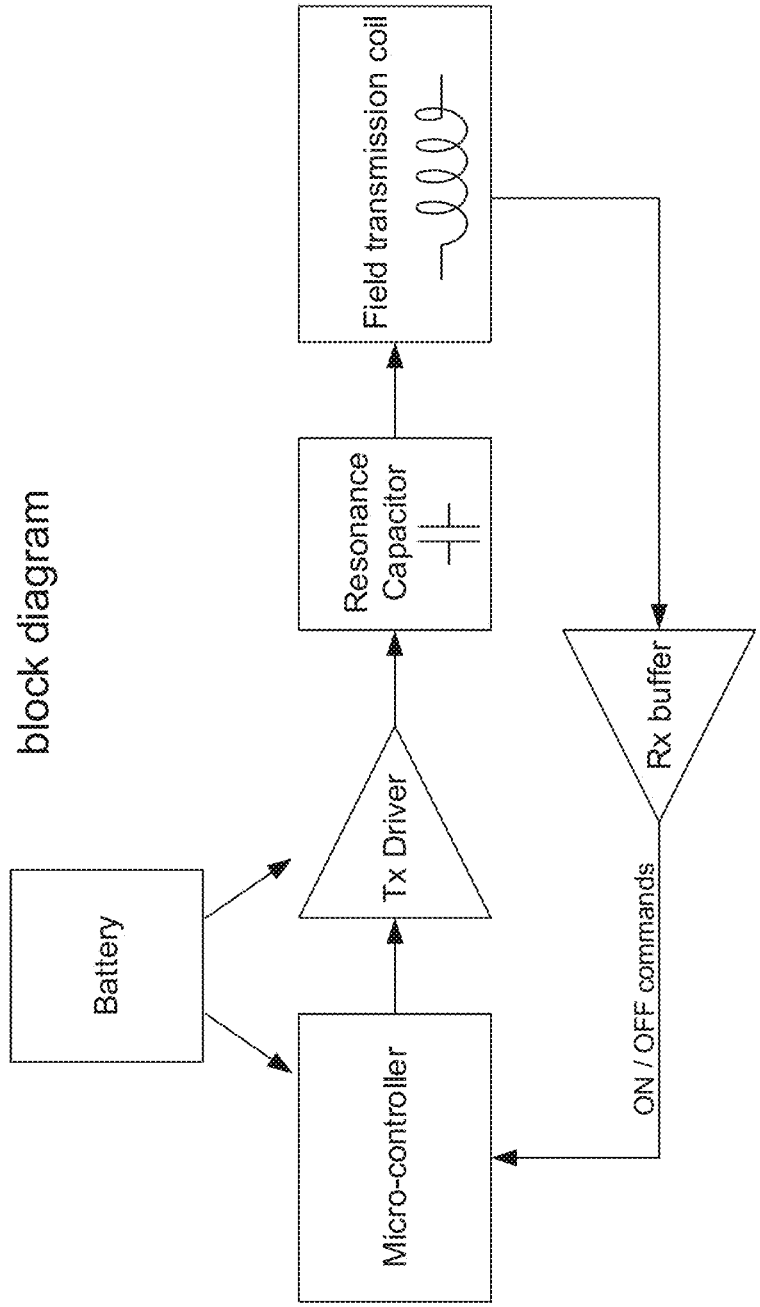
Figure 16:
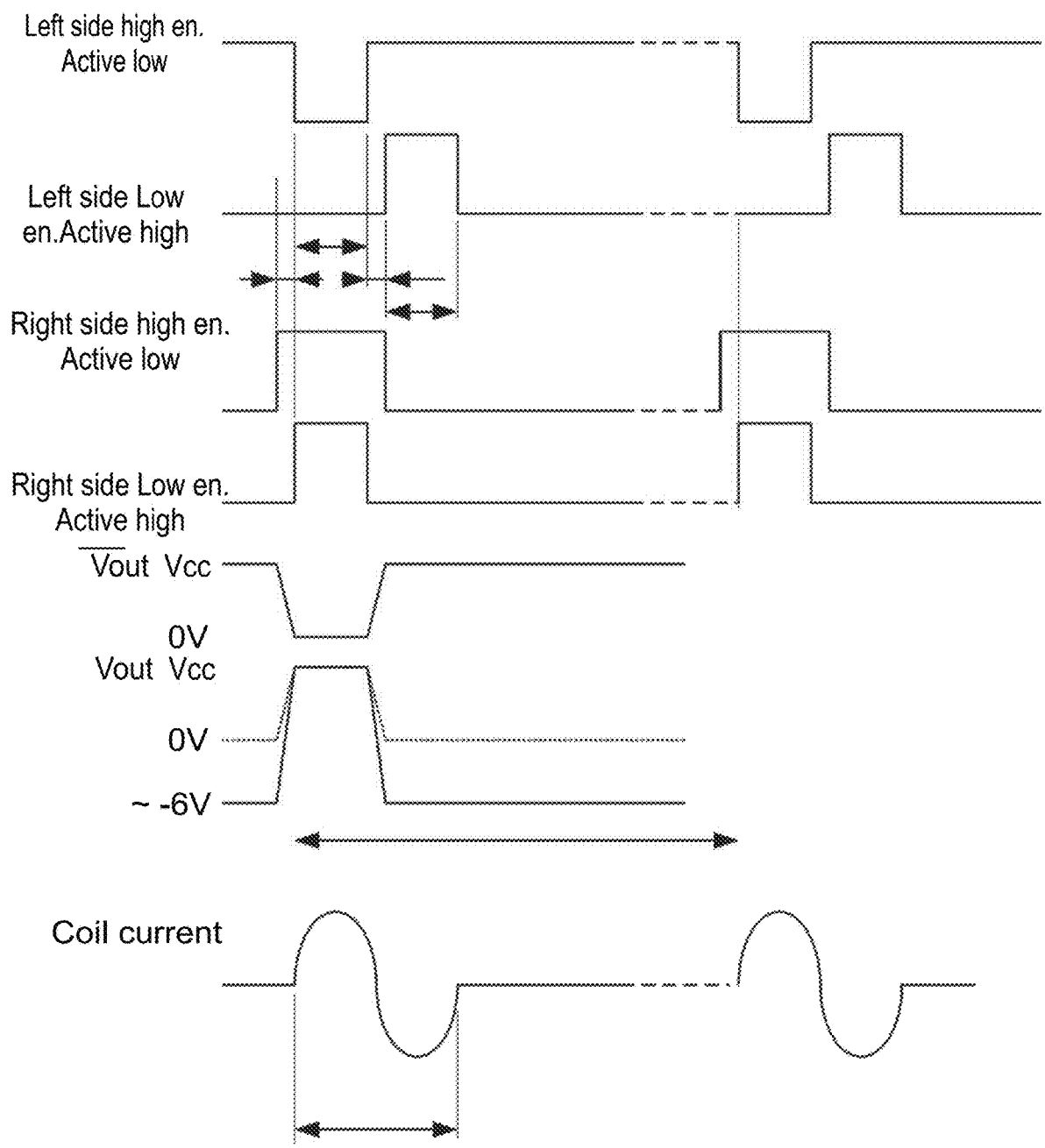

FIGS. 14 and 15 are block diagrams showing how an electronic patch can use its coil as a radio receiver to receive communications, according to an exemplary embodiment of the invention; and FIG. 16 is a plot of square wave signals that are used to drive the generation of pulsed electromagnetic fields by an electronic patch, as well as a plot of the current generating the pulsed fields, according to an exemplary embodiment of the invention.

DESCRIPTION OF SPECIFIC EMBODIMENTS OF THE INVENTION

An aspect of some embodiments of the invention concerns an electronic patch that produces pulsed electromagnetic fields to promote tissue healing, and that optionally uses a resonant energy-saving circuit to recycle field energy from one pulse to the next, potentially allowing a smaller and thinner battery to be used, allowing the patch to be thin and flexible.

An aspect of some embodiments of the invention concerns an electronic patch that is placed on the outside of the body, with a coil, or two coils, placed for example on different sides of a limb, or more than two coils, that repeatedly produce pulsed magnetic fields at a target site adjacent to the patch inside the body. The pulsed magnetic fields induce a changing electric field at the target site, which is believed to improve healing of the tissue. The resonant circuit very efficiently transfers the electromagnetic field energy of each pulse into electrostatic energy of a capacitor, which can be stored with almost no losses and converted into electromagnetic field energy again in the next pulse. For example, more than 50% of the field energy is recycled at each pulse, or more than 90%, of more than 95%, or more than 99%, or more than 99.9%. Optionally, the field energy is converted and stored so efficiently that the dominant energy losses are the ohmic losses from the coil.

The resonant circuit also operates in such a way there is no current, or very low current, in the coil between pulses, so the ohmic losses are almost as low as they can be. For example, the current between pulses is in the range from 30 nA to 3 $\mu$A, while the peak current during a pulse is in the range from 0.1 mA to 25 mA, or 25 mA to 3 A. Low current between pulses may occur because each pulse lasts for only about one half of a wave cycle or one wave cycle at the LC resonance frequency of the coil and the capacitor.

In an exemplary embodiment of the invention, at the beginning of a pulse, the current in the coil is zero, and the capacitor is charged up to an operating voltage that it maintains between pulses. The voltage across the capacitor and coil, in series, is suddenly reversed. Current starts to build up in the coil, and the capacitor starts to discharge, and to charge up with the opposite polarity. The pulse ends when the capacitor is charged up to its operating value with the opposite polarity, and the coil current has returned to zero. The coil current remains at or very close to zero, with no or almost no energy losses, until another pulse is initiated by reversing the voltage again.

Optionally, radiative losses are potentially negligible, because the resonant frequency, which is the dominant frequency of the pulses, is not too high, for example between 10 kHz and 100 kHz, with the coil not much more than 100 mm wide, very small compared to a wavelength at 10 or 100 kHz. Optionally, the pulses are very short compared to the time between pulses, for example the duty cycle, the ratio of pulse times to total time, may be less than 10%, or less than 1%, or less than 0.2%. For example, there may be between 2 and 100 pulses per second. In addition, the device may operate for only a few hours each day, for example between 2 and 10 hours a day.

Very efficient use of energy makes it possible to use a battery of relatively low energy storage capacity to power the patch for the full course of treatment, which may be 3 to 20 weeks, for example. Optionally, there is no need to recharge the battery during this time, and a non-rechargeable battery is optionally used. Not needing to recharge the battery has the potential advantage that the patient doesn't have to make an appointment for that purpose, saving time for the patient and for medical personnel. Furthermore, non-rechargeable batteries are cheaper, and may be smaller for the same capacity, than rechargeable batteries.

The battery may store less than 2000 milli-amp hours of charge, or between 30 and 2000 milli-amp hours, or less than 250 milli-amp hours, at a voltage between 1.5 and 20 volts, or between 1.5 and 6 volts, for example 1.55 volts, 2 volts, 3 volts, 3.6 volts, or 5 volts. Relatively low voltage batteries may be used if the energy storage requirements are low. Optionally, the battery is less than 5 mm thick, or less than 3 mm thick, or less than 2 mm thick, and fits inside the coil. With such a thin battery, the patch itself can be very thin, for example between 2 and 10 mm thick, optionally less than 5 mm thick, or less than 3 mm thick, or less than 2.5 mm thick.

Optionally the patch is made of a flexible material, such as silicone, or polyimide, or liquid crystal polymer, and is flexible enough and stretchable enough to conform to the surface of a patient's body adjacent to the site of the fractured bone. For example, the radius of curvature of the patch, when it is conforming to the surface of the body, is 2 cm, or 3 cm, or 5 cm, or 10 cm, or 20 cm, and has cylindrical curvature, or positive curvature like the surface of a sphere, or negative curvature like a saddle-shape. Even if the battery is rigid, and the electronics are comprised in a rigid board, the patch can still be relatively flexible because the small size of the battery makes it possible to provide enough space between the battery and the electronics where the patch can bend. Optionally, the electronics comprises printed electronic components that are also flexible. Optionally, a flexible battery is used.

The flexibility of the patch may make it possible for the patch to be directly in contact with the patient's skin, under a cast, if any, which may allow further reducing the current, and the ohmic losses, needed to produce fields of a given amplitude at the bone fracture or other treated tissue. Furthermore, having all the components in a single thin patch may make the treatment more pleasant for the patient, who need not even notice or think about the patch, especially when it is under a cast, in contrast to prior art which uses bulky and very noticeable components, at least some of them outside the cast. Optionally, the patch is under the cast, and has sensors to measure the pressure of the cast. For example, a pressure sensor may be used to measure the pressure, or a blood oxygen sensor in the patch, placed directly against the patient's skin, may indicate if the pressure is too high, interfering with blood circulation. Optionally, a communications link, for example a wireless link, may provide data from these sensors, under the cast, to medical personnel. Alternatively, the low blood oxygen level is communicated to medical personnel by lighting up a warning light.

Healing bone fractures is an important application of the patch, but it is potentially useful also for healing other kinds of tissue, including muscles, tendons, cartilage, and skin (scar tissue), and it may improve the quality of healing, as well as its speed. For example, it may improve the elasticity of healed tendons.

An aspect of an exemplary embodiment of the invention concerns an electronic patch with two coils, wrapped at least partly around a cylindrical body part, for example an arm, leg, hand, foot, neck, pelvis or rib cage, with the two coils on different sides of the body part, optionally under a cast. The coils optionally operate in two modes. In one mode, current passes through both coils, and together they produce an electromagnetic field at the bone fracture site, or soft tissue target site, inside the body part. In the other mode, which optionally operates only occasionally, current flows only through one of the coils. The magnetic flux pulse produced by that coil links the second coil, and induces an emf (electromotive force) voltage in that coil, according to Faraday's law, which is detected by the second coil. The measured voltage in the second coil, for a given current in the first coil, provides information on the mutual inductance of the two coils, which in turn provides information on the distance between them, or at least on changes in the distance between them.

In some embodiments of the invention, the information on emf voltage is used to produce electromagnetic fields of a specified amplitude at the bone fracture site by adjusting the current in the coils, even if it is not known in advance exactly how wide the cylindrical body part is, and how far from the coils the target site is. Once the induced voltage in the second coil has been measured, the electronic patch can return to operating in the mode with current flowing in both coils, and the current in both coils set at a level that is calculated to produce the specified level of electromagnetic fields at the target site, whose distance from the coils may be estimated based on the emf voltage. In some embodiments of the invention, the second coil is only used for measuring the emf voltage induced by the first coil, and only the first coil ever has current in it, to produce electromagnetic fields.

Optionally, the induced emf voltage on the second coil is repeatedly measured over time, and the treatment proceeds. If the coils are getting further apart, this may indicate increased swelling of the body part, which might not be visible underneath the cast, and may indicate that the bone is not healing properly, and that some medical intervention is needed. If the coils are getting closer together, this may indicate that the arm is shrinking more quickly than expected, and the cast is loose, and is no longer effectively immobilizing the body part. In this case, it may be necessary to remove the cast and replace it. If the arm is shrinking faster than expected, that may also indicate greater than expected wasting of muscle, which may call for some medical response.

An aspect of some embodiments of the invention concerns an electronic patch, flexible enough and of suitable size to wrap at least partly around a body part while generally conforming to the surface of the body part, comprising two flexible coils, located on different sides of the body part when the patch is wrapped around the body part, that produce pulsed electromagnetic fields at a target site inside the body part, to promote tissue healing.

An aspect of some embodiments of the invention concerns an electronic patch, comprising a substrate on which is mounted at least one coil with an open region in the center at least 20 mm in diameter in all directions, the coil producing pulsed electromagnetic fields at a target site inside the body, to promote tissue healing, and one or more electronic elements that are substantially opaque to medical x-rays, wherein the opaque electronic elements are mounted away from the center of the open region.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flexible Electronic Patch

Figure 1:
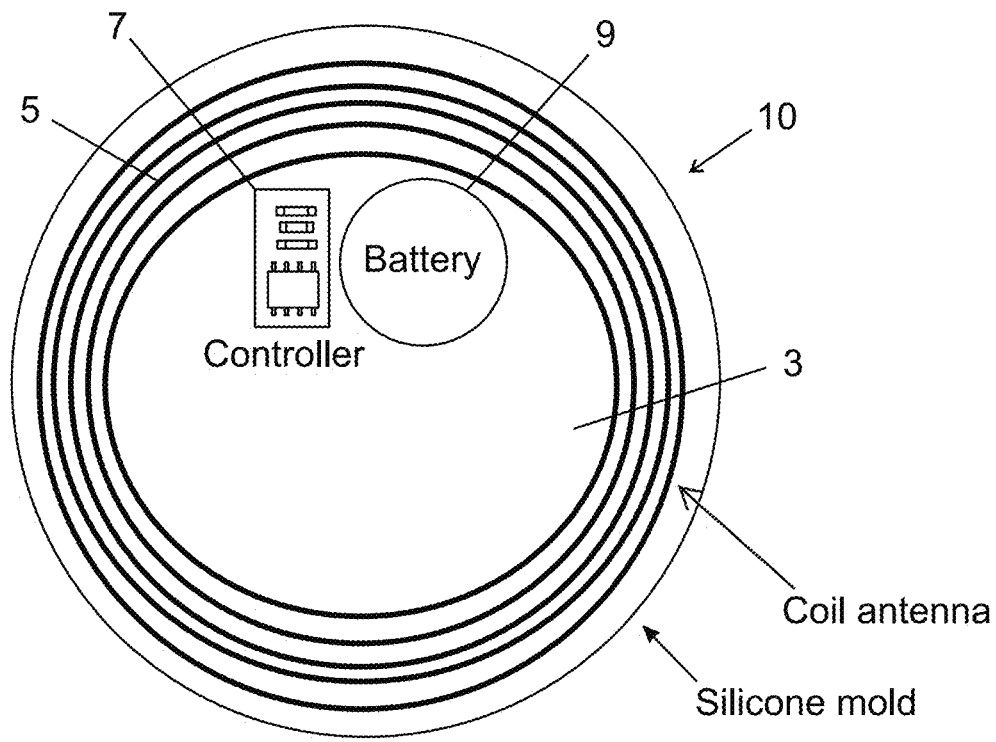
FIG. 1 is a schematic top view of an electronic patch with a single coil, according to an exemplary embodiment of the invention.

Referring now to the drawings, FIG. 1 schematically illustrates a top view of an electronic patch 10 for treating body tissue with electromagnetic fields, according to an exemplary embodiment of the invention. The components of the patch are optionally imbedded in a substrate 3, made from a flexible bio-compatible material, such as silicone, formed for example in a mold. The components include a coil 5, which in the case of patch 10 is circular, and goes around the outside of the patch, which is 80 mm in diameter. In other embodiments of the invention, for example designed to be used on different parts of the body, the patch and the coil may be a different size or shape.

An electronics package 7, and a battery 9, are optionally located inside the coil. The battery supplies electric power to the coil, through the electronics package, and the electronics package includes circuitry that controls pulses of current passing through the coil, including energy saving circuitry that recycles most of the field energy in each pulse, so that the battery for the most part may only have to supply energy to make up for ohmic losses. The battery and electronics package need not be located inside the coil, but this arrangement has the potential advantage of allowing the patch to be more compact, because the size of the coil may be based on the area and depth of body tissue that is being exposed to the electromagnetic fields, and turns of coil that have much smaller radius will generally produce electromagnetic fields that do not extend as deeply or as widely.

Optionally, the battery, if it is small enough, is located off to the side of the center of the coil, or the battery is not inside the coil at all, in order to avoid having the battery block an x-ray view of fracture site or other target site.

It should be understood that the coils shown in FIG. 1, and in the other drawings, are drawn schematically, with a few concentric circles representing multiple turns. Also, the connections between different turns, and the connections between different coils or between the coils and other components, are not necessarily shown.

Figure 2:
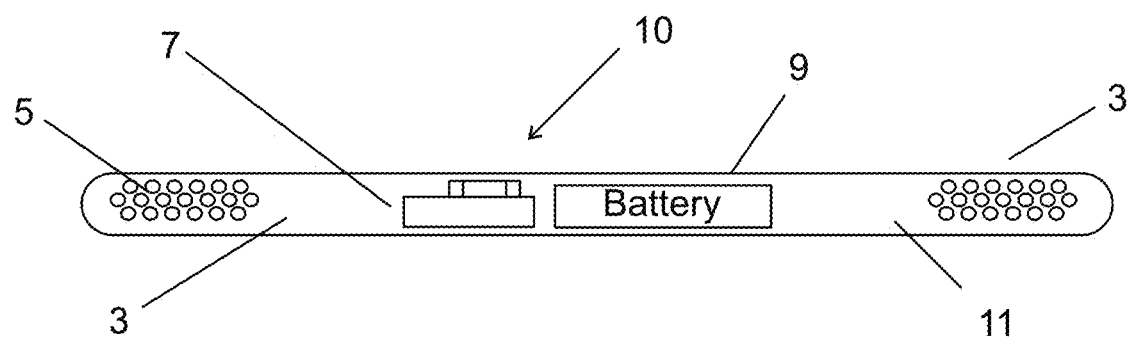
FIG. 2 is a schematic side view of the electronic patch shown in FIG. 1.

FIG. 2 schematically shows a side cross-sectional view of patch 10. The patch is, for example, 6 mm thick, and this thickness is largely dependent on how thin the battery is. The battery in patch 10 is about 3.5 mm thick. The more efficiently the patch uses energy to create the electromagnetic fields, the less storage capacity the battery needs, and the thinner the battery can be, and the thinner and more flexible the patch can potentially be. For example, the patch is optionally only 5 mm thick, or 4 mm, or 3 mm, or 2.5 mm, or 2 mm, or less, and the battery is optionally less than 3 mm or less than 2.5 mm or less than 2 mm thick. Optionally, the battery is not recharged during the course of treatment by the electromagnetic fields, and optionally the battery is not even rechargeable, and in this case the battery needs enough storage capacity to power the patch for the entire period of treatment. For example, the battery has between 30 mA-hours and 2000 mA-hours of storage capacity, with a voltage between 1.5 volts and 20 volts.

If the battery is rigid, then it is potentially advantageous if the battery is not too wide, for example no wider than 25 mm, especially in a direction where the patch may have to bend in order to conform to a surface of the patient's body. It is also potentially advantageous if the electronics package is not too wide, if it is rigid, for example not wider than 25 mm, and if there is at least 1.5 mm between the battery and the electronics package, if they are arranged along a direction that the patch has to bend. This can help to ensure that the patch is flexible enough to conform at least generally to a surface of the patient's body, adjacent to the body tissue that is being exposed to the electromagnetic fields, as well as to ensure that the patch is comfortable for the patient to wear.

In some embodiments of the invention, the electronics package is not rigid, but, for example, comprises flexible printed electronics parts, manufactured, for example, by thinned die thermocompression laminated onto liquid crystal polymer (LCP) films. In some embodiments of the invention, the battery may be flexible, for example, a flexible polymer battery may be used. However, a polymer battery may not have enough storage capacity to last for the entire course of treatment without being recharged, and a polymer battery may not be rechargeable. In general, any type of battery that is sufficiently small and thin, and has sufficiently high storage capacity may be used, including alkaline, silver, lithium, nickel oxyhydroxide, and zinc air batteries.

There is a table listing battery types, with dimensions in mm and capacity in mA-hrs, available at www(dot)en(dot)m(dot)wikipedia(dot)org/wiki/List_of_battery_sizes>. Promising batteries are those with relatively low height, for example less than 3 mm or not much more than 3 mm, and relatively high capacity, for example more than 100 mA-hrs, or not too much less than that. For example, the CR2032 is 3.2 mm high and has a capacity of 225 mA-hrs, the CR2016 is 1.6 mm high and has a capacity of 90 mA-hrs, the CR2025 is 2.5 mm thick and has a capacity of 160 mA-hrs, the CR2320 is 2.0 mm thick and has a capacity of 110 mA-hrs, the CR2325 is 2.5 mm thick and has a capacity of 165 mA-hrs, and the CR2330 is 3.0 mm thick and has a capacity of 265 mA-hrs.

Renata SA of Itingen, Switzerland sells a flexible Li/MnO$_2$ battery called the CP042350, which might be suitable. It is only 0.42 mm thick, but has an area of 50 mm by 23 mm, and a storage capacity of only 28 mA-hrs. A few of them might have enough storage capacity, but might take up too much area. And if they were stacked, they might not be flexible enough.

In some embodiments of the invention, more than one battery may be used. It should be understood that whenever a battery is referred to herein, more than one battery may be used. Multiple batteries may be connected in series, to increase the voltage, and/or in parallel, to increase the current. In either case, using multiple batteries can increase the total battery storage capacity. A potential advantage of using multiple batteries is that the battery storage capacity may be increased, without having a large rigid volume, since the individual batteries can be spaced somewhat apart in the flexible substrate, to conform to the body surface of the patient.

Optionally, the electronic patch is water resistant. For example, it can withstand exposure to water for 24 hours without being damaged, or 100 exposures to water for 30 minutes each, which would allow the patient to take a shower twice a day during a treatment that is 50 days long. Optionally, the patch is completely water proof, and can withstand exposure to water for 10 days, 20 days, 40 days, 50 days, or 120 days, without being damaged.

Figure 3:
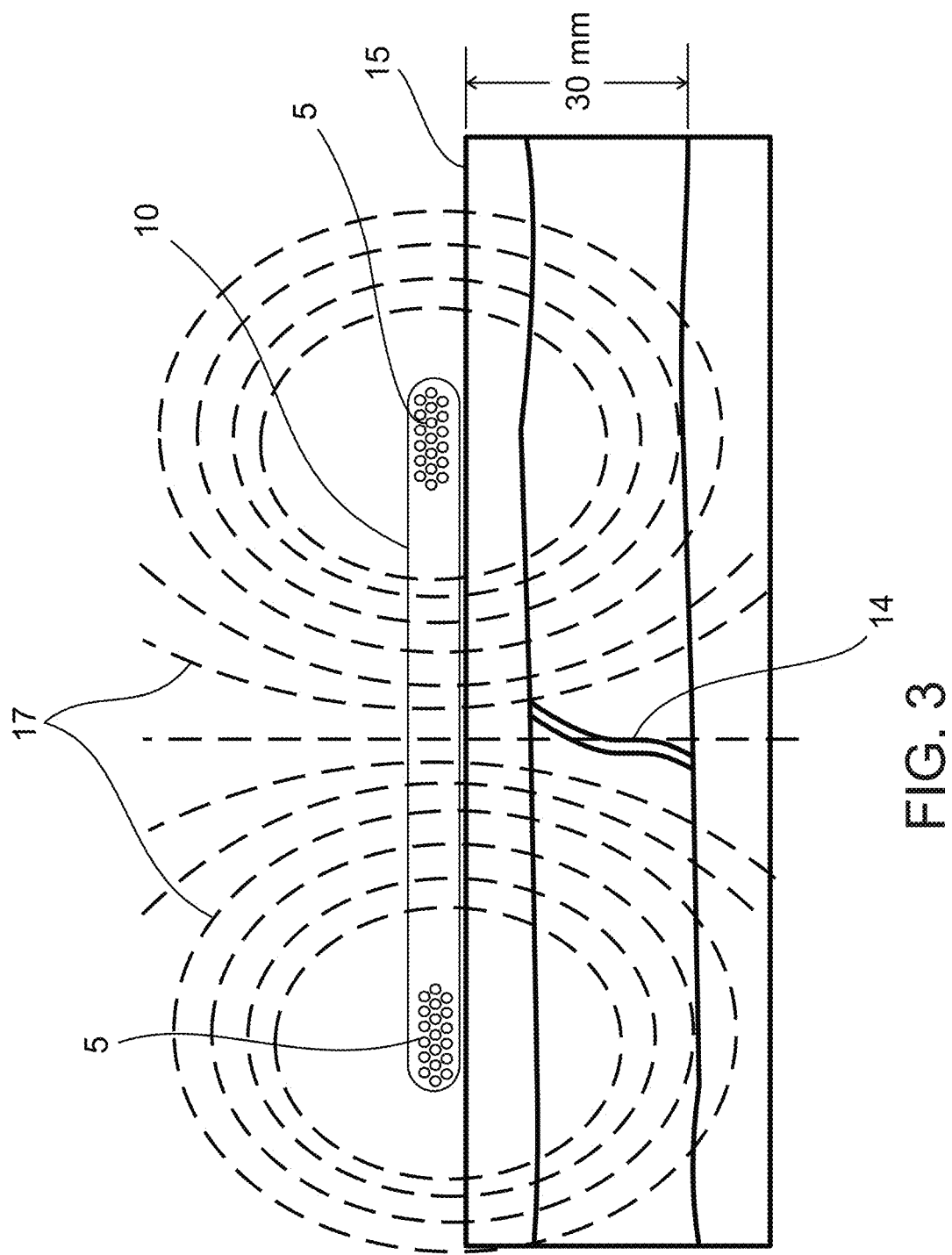
FIG. 3 is a schematic side view of the electronic patch shown in FIG. 1, in place on the surface of a patient adjacent to a fractured bone site, showing magnetic field lines of the electromagnetic field generated by the coil.

FIG. 3 schematically shows electronic patch 10 in place on a surface of a patient's body, adjacent to a fracture 14 in a bone. Current in coil 5 produces an electromagnetic field 17 that extends into the patient's body, reaching fracture 14. The furthest part of fracture 14 is about 30 mm beneath patch 10, which is smaller than the radius of coil 5, and the electromagnetic field reaches that far, without much attenuation compared to its value at the surface of the patient. It should be understood that the magnetic field lines shown in FIG. 3, and in other drawings, are drawn schematically, roughly representing the shape of the field, but they are not based on accurate magnetic field calculations.

The peak current in coil 5, and the peak current in other patches shown herein, is optionally between 0.1 and 0.5 mA, or between 0.5 and 2 mA, or between 2 and 5 mA, or between 5 and 25 mA, or between 25 and 100 mA, or between 100 and 500 mA, or between 500 mA and 1 A, or between 1 and 3 A, or less than 0.1 mA or more than 3 A. The peak magnetic field produced at the target site is optionally between 2 and 5 microtesla, or between 5 and 10 microtesla, or between 10 and 20 microtesla, or between 20 and 50 microtesla, or between 50 and 100 microtesla, or less than 2 microtesla or more than 100 microtesla.

Figure 4A:
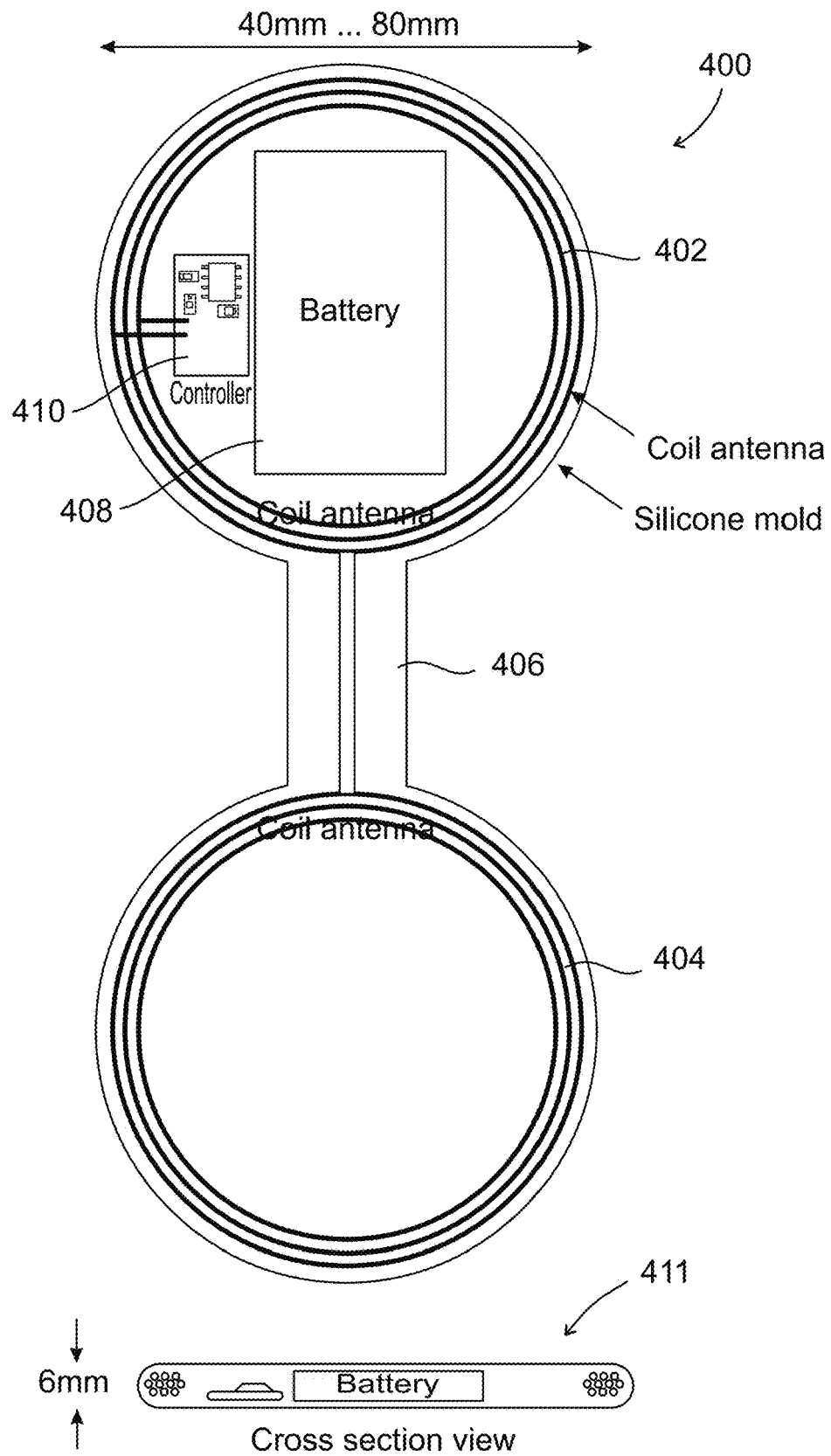
FIG. 4A is a schematic top view of an electronic patch with two coils, in a flat unwrapped configuration before being placed on a patient, according to an exemplary embodiment of the invention.
Figure 5:
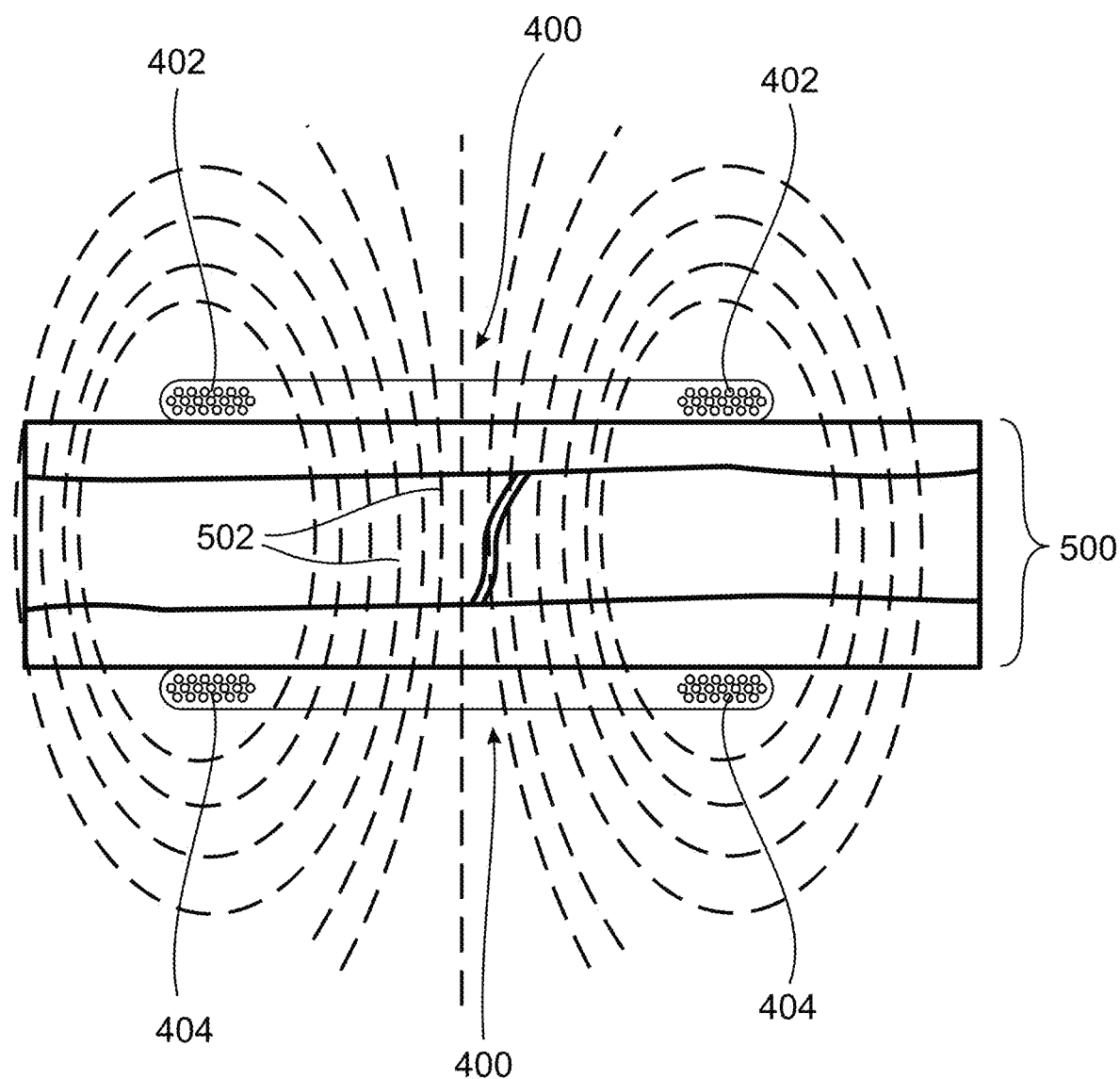
FIG. 5 is a schematic side view of the electronic patch shown in FIG. 4A, FIG. 4B, or FIG. 4C, wrapped around the limb of a patient with a fractured bone site, showing magnetic field lines of the electromagnetic field generated by the coils.

FIG. 4A schematically shows an electronic patch 400 with two circular coils 402 and 404, each imbedded in silicone, with a flexible strip of silicone 406 connecting them. Patch 400 is designed to wrap at least part way around a cylindrical body part, for example an arm, hand, leg, foot, pelvis, rib cage or neck, with coil 402 on one side of the body part, and coil 404 on another side of the body part, optionally on an opposite side from coil 402, optionally facing coil 402. When they are in this position, the two coils produce magnetic fields inside the cylindrical body part, between the coils, that are oriented in approximately the same direction, and add up, similar to the magnetic field produced by Helmholtz coils. FIG. 5 shows coils 402 and 404 in place on opposite sides of cylindrical body part 500, producing a magnetic field 502 inside the body part.

Having two coils on different sides of the body part, producing the electromagnetic fields at the target site inside the body part, has the potential advantage that the fields are more uniform, and less current is required, and hence lower power in required, to produce the same field. For example, if the target site is a fractured bone site, and the fracture extends across the width of a bone, then a coil at one side of the bone can more efficiently produce fields on that side of the bone, and a coil at the other side of the bone can more efficiently produce fields on that side of the bone. So the fields are potentially produced more efficiently than they would be by only one coil, whichever side it is located on.

Optionally, coil 402 and coil 404 are connected together, for example in series or in parallel, such that a current going through one of the coils in a given direction will always result in current going through the other coil in the same direction when patch 400 is folded over with the two coils facing each other. Alternatively, coils 402 and 404 operate independently of each other, either with a single electronics package with a controller that independently controls the current in each coil, or with separate electronics packages for each coil, and optionally with a separate battery for each coil. But FIG. 4A shows the case where both coils are controlled by a same electronics package 410, and powered by a same battery 408. Even if the currents in the two coils are controlled independently, they normally operate with the current going in the same direction around the coil, when the two coils are facing each other.

In an embodiment of the invention shown below in FIG. 9, with a configuration similar to that of patch 400 in FIG. 5, in one mode of operation, only the first coil has current flowing in it, and the second coil is used to measure the emf induced by the first coil. A potential advantage of controlling the currents separately in the two coils is that it is possible to run the patch in the mode shown in FIG. 9.

In some embodiments of the invention, the two coils may be oriented at different orientations, rather than facing each other. In some embodiments there are three or more coils, which may be oriented in various ways. A potential advantage of the configuration shown in FIG. 5, is that the magnetic field contributed by both the coils adds up inside the body, so the field inside the body may be greater, for a given ohmic loss in the coils, than for other arrangements of coils.

A side cross-sectional view 411 of patch 400, showing the coils, battery, and electronics package, is shown at the bottom of FIG. 4A.

Figure 4B:
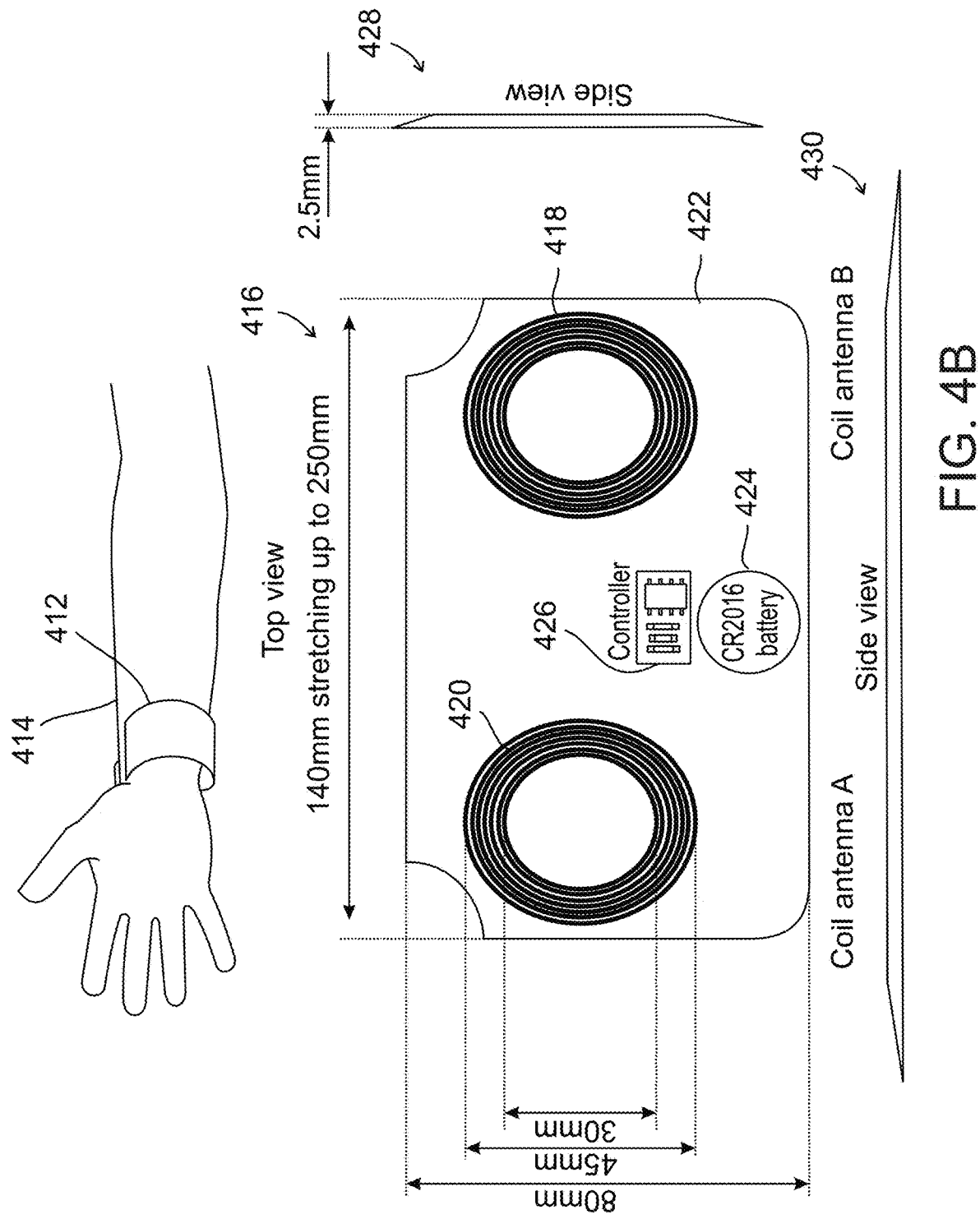
FIG. 4B is a schematic top view of another design for an electronic patch with two coils, in a flat unwrapped configuration, according to an exemplary embodiment of the invention.

An alternative design for a two-coil electronic patch 412 is shown in FIG. 4B. The patch is designed for use around the wrist, to treat fractures of the distal radius, and is shown partly wrapped around a wrist 414 of a patient. The patch is not wrapped completely around the wrist and joined together, which gives the wrist room to expand if it becomes swollen, and in addition it is made of a stretchable material, and can expand from a length of 140 mm to 250 mm. A top view 416 of the patch shows a circular coil 418 and a circular coil 420, embedded in a flexible elastic substrate 422. A CR2016 battery 424, and an electronic package 426, which includes a controller, are located between the two coils but closer to the edge of the patch, vertically displaced from the centers of the coils as seen in the drawing. Putting the battery and electronics package outside the coils has the potential advantage that they will not block a view of the fracture in an x-ray image, if an x-ray image is taken in order to examine the fracture while the patient is wearing the electronics patch. If an x-ray image is taken looking through the holes of the coils at the fracture site, i.e. in an anterior-posterior direction, then the image will not be blocked by the battery or the electronics package as long as they are not in the center of the hole. In addition, if the battery and electronics package are displaced vertically from the centers of the holes, then the view of the fracture site, which is right between the coils, will also not be blocked if the x-ray image is taken from a lateral direction, facing in a direction perpendicular to the cylindrical axis of the body part, but parallel to the plane of the coils. It should be understood that "vertical" and "horizontal" refer here to directions in the plane of the unwrapped patch, with the horizontal direction being the direction separating the two coils, and the direction along which the patch wraps around the body part. They have nothing to do with the orientation of the patch and the body part in space.

In some embodiments of the invention, the coils have relatively low opacity to x-rays, at wavelengths of interest for medical imaging, and/or they have a similar opacity to x-rays as the substrate has, so the coils do not interfere very much with x-ray images of the wrist.

Figure 4C:
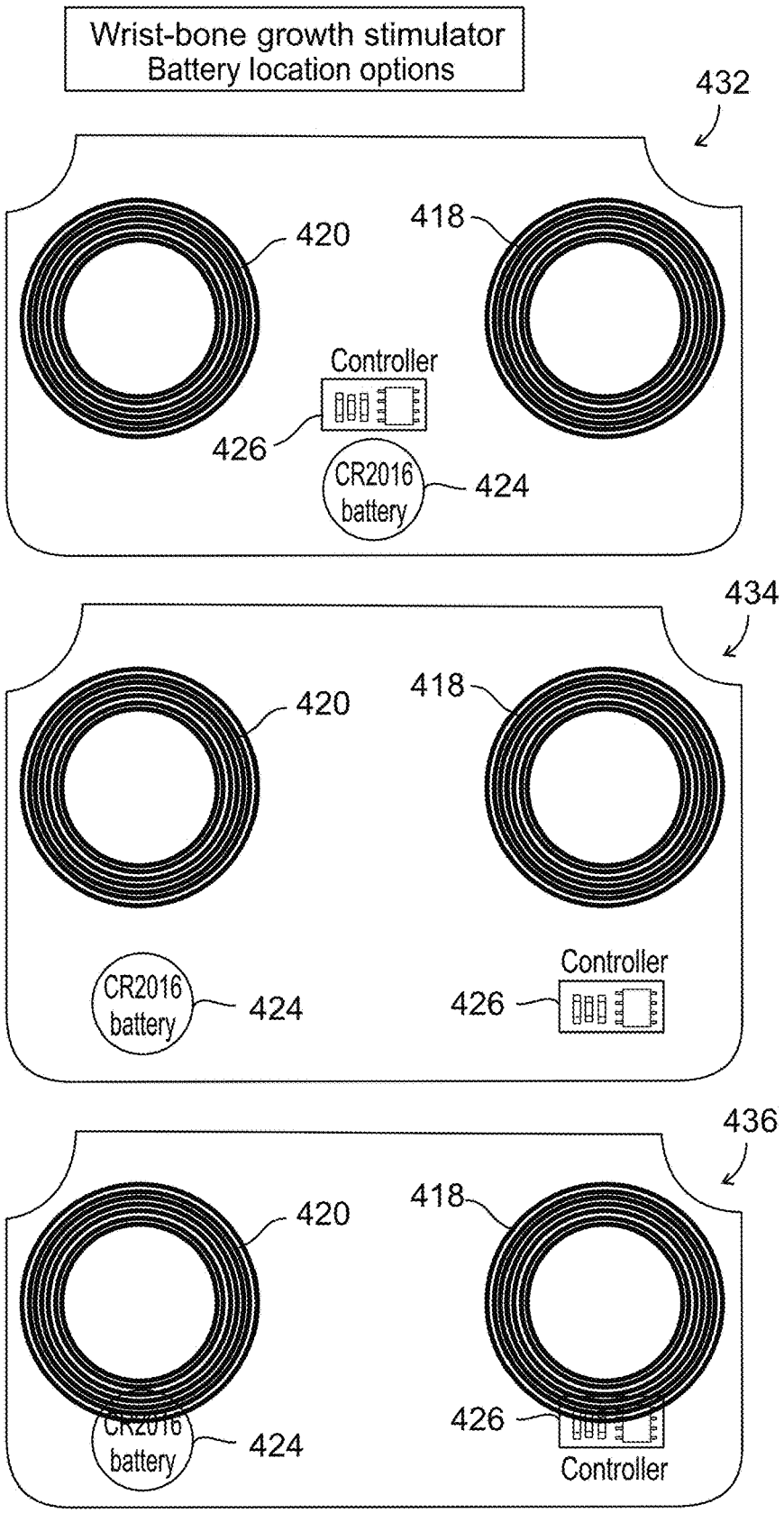
FIG. 4C is a schematic top view of several variants on the design of FIG. 4B, with the battery and electronics package placed at different positions, according to an exemplary embodiment of the invention.

Two side views 428 and 430 show the small thickness of the patch, only 2.5 mm. FIG. 4C compares electronic patch 412, shown in FIG. 4B, with two alternative designs. Top view 432 shows the same electronic patch as shown in FIG. 4B, and top views 434 and 436 show two other designs, with a different placement of battery 424 and electronics package 426. In all three designs, the same coils 418 and 420 are used, with outer diameter of 45 mm and inner diameter of 30 mm. In view 432, the battery and electronics package are between the two coils, but displaced vertically, closer to the edge of the patch. Putting the battery and electronics package closer to the edge of the patch, i.e. displaced vertically, may keep them from interfering with the visibility of a fracture in the bone, in an x-ray taken from any angle, lateral or anterior-posterior. In this design the patch is 80 mm wide (the vertical direction in FIG. 4C). In view 434, the battery and the electronics package are each between one of the coils and the edge of the patch, well away from interfering with an x-ray image of the fracture. In this design, the patch is a little wider than in view 432, 90 mm. In view 436, the battery and the electronics package each overlap the coil that they are near. This patch is narrower than the other designs, only 70 mm, but thicker, 3.5 mm as opposed to 2.5 mm for the patches shown in views 432 and 434, to accommodate the overlap.

Exemplary Energy-Saving Resonant Circuit

Electronics package 7, in electronic patch 10 in FIGS. 1 and 2, and the similar electronics package 410 in electronic patch 400 in FIG. 4A, and electronics package 426 in FIGS. 4B and 4C, optionally includes a resonant energy saving circuit. The energy saving circuit includes a capacitor in series with the coil, and pulse generating circuitry, which repeatedly changes the voltage across the capacitor and coil, to produce pulses of current in the coil. The pulse generating circuitry may comprise a controller, for example a digital controller, that is programmed to make the changes in voltage at certain times, or the changes in voltage may be generated periodically by an analog circuit with some non-linear elements. Initially, or at least after the pulse generating circuitry has been operating for several pulses and reaches a steady state, the capacitor is charged up to a certain voltage before a pulse is initiated. When the pulse is initiated, the electric energy of the capacitor is discharged into the magnetic field energy of the coil, and is then recycled back to the capacitor, where it remains until the next pulse is initiated. Ideally, almost all of the energy of the capacitor is available for producing the electromagnetic field of the coil, and almost all of the electromagnetic field energy of the coil is recycled back to the capacitor at the end of a pulse, with very little dissipation of energy. There are ohmic losses in the coil, but these will be relatively small, compared to the energy cycling between the coil and the capacitor, if the resistance R of the coil is much less than $(L/C)^{1/2}$, where L is the inductance of the coil and C is the capacitance of the capacitor. For example, R is less than $(L/C)^{1/2}$ by at least a factor of 10, or at least a factor of 100, or at least a factor of 1000. Radiative losses from the coil will be negligible if the resonance frequency $(LC)^{-1/2}$ is small compared to the speed of light divided by the coil diameter, which is 3 GHz for a coil 100 mm in diameter, while the resonance frequency is typically between 10 and 100 kHz. There may also be some energy losses from eddy currents induced by the electromagnetic field in any conductors that the field comes in contact with, including the body of the patient. Any energy losses have to be supplied by the battery.

An example of a resonant energy-saving circuit is described in published US patent application US2018/0015295-A1, "Bone Enhancement Device and Method," to Moshe Neumann, Roni Daffan, and Joseph Shechter, published Jan. 18, 2018, and will be described here in FIGS. 6, 7, 8, 13 and 16. Further details of how this resonant energy-saving circuit may be implemented, and in particular how the pulse generating circuitry may be implemented, may be found in that publication.

Figure 6:
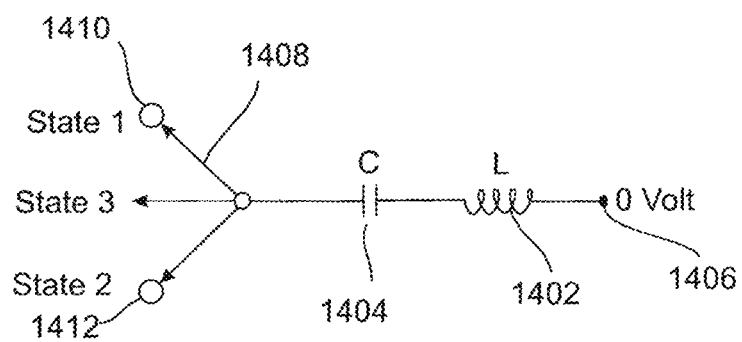
FIG. 6 is a schematic circuit diagram illustrating the principle of operation of a resonant energy saving circuit that can be used for the electronic patch of FIG. 1 or FIG. 4A, FIG. 4B, or FIG. 4C, according to an exemplary embodiment of the invention.
Figure 7:
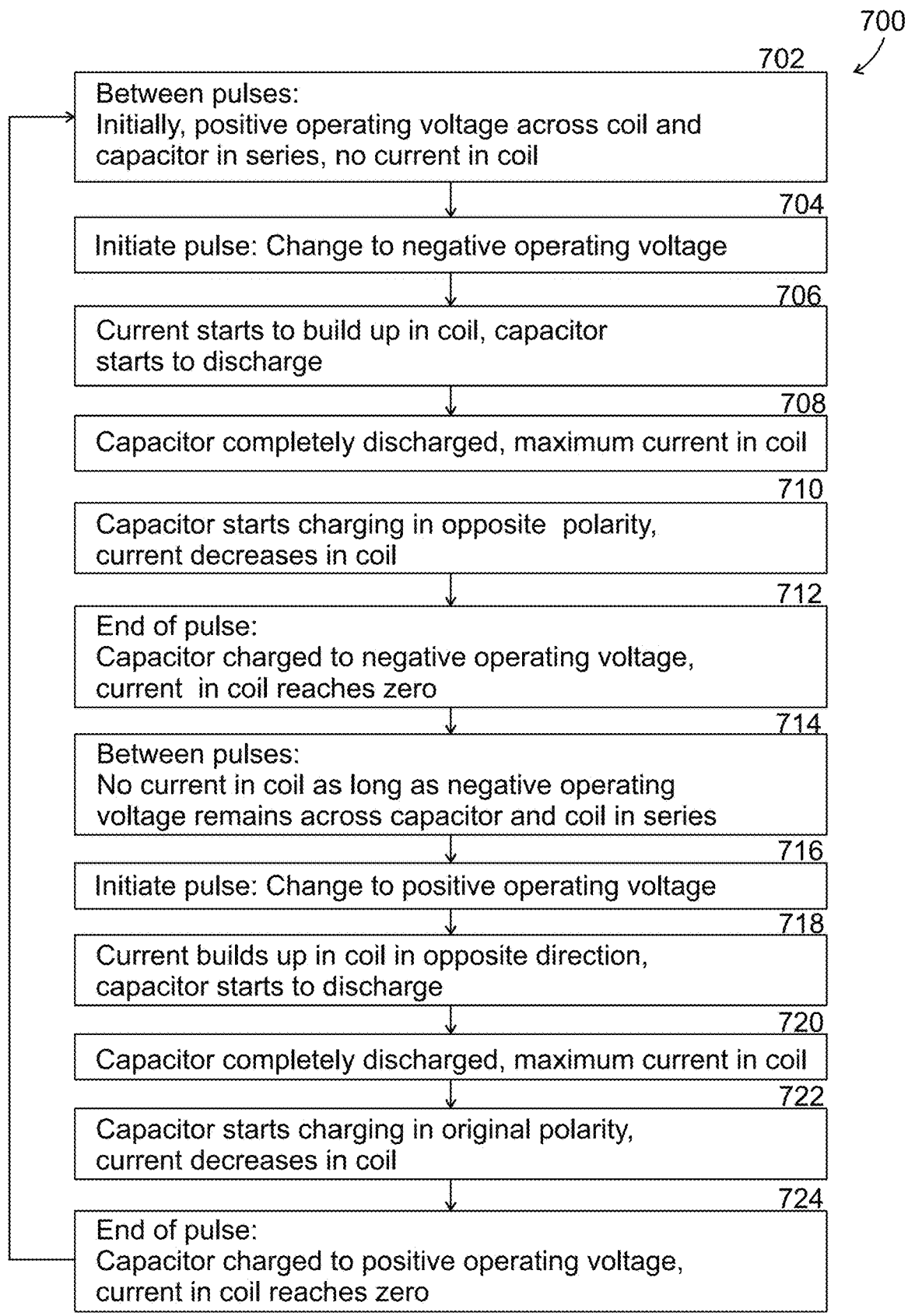
FIG. 7 is a flowchart showing the operation of the energy saving resonant circuit of FIG. 6.
Figure 8:
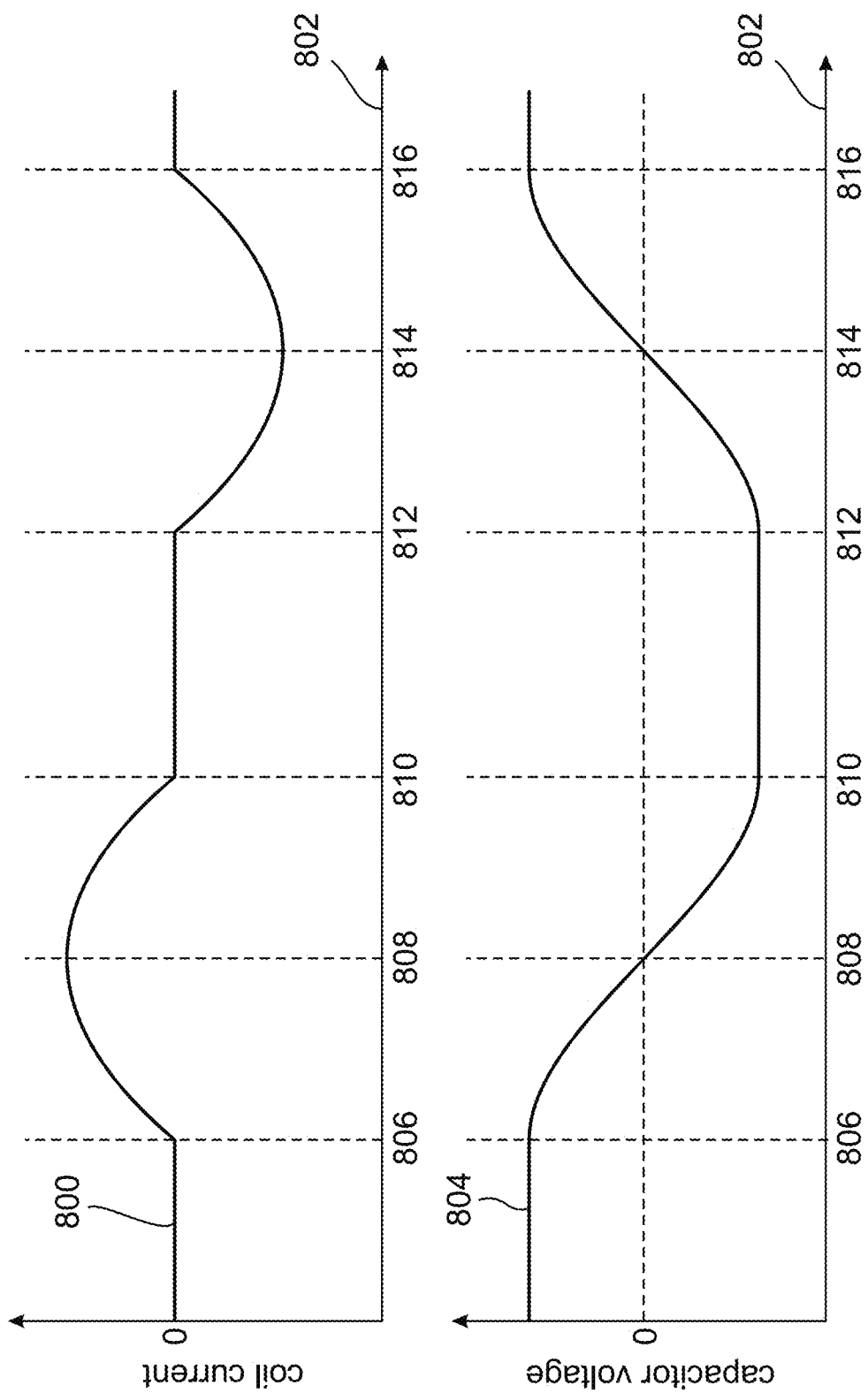
FIG. 8 is a schematic plot of the current through the coil, and the voltage across the capacitor, as a function of time, during the operation of the resonant energy saving circuit of FIG. 6, for a few pulses.

FIG. 6, schematically shows a circuit diagram for a portion 600 of such a resonant energy-saving circuit, including a coil 1402 with inductance L, a capacitor 1404 with capacitance C, a zero-voltage terminal 1406, and a terminal 1408 with a voltage controlled by the pulse generating circuitry, not shown in FIG. 6. The changes to the voltage 1408 are shown schematically by terminal 1410, which has a positive operating voltage, for example equal to the battery voltage and terminal 1412, which has a negative operating voltage, for example equal to the battery voltage in magnitude. Initially, at least once several pulses have been initiated and the circuit has reached a steady state, terminal 1408 is set to the positive operating voltage of terminal 1410, as shown in box 702 of flowchart 700 in FIG. 7, and capacitor 1404 has a positive voltage equal to the operating voltage, and there is zero voltage across coil 1402, and no current flowing in the coil. To initiate a pulse, terminal 1408 is set to the negative operating voltage of terminal 1412, at box 704 of flowchart 700. At first, capacitor 1404 remains charged at the same positive operating voltage that it had before, and coil 1402 now has a voltage across it equal to nearly twice the operating voltage, if the positive and negative operating voltages are equal in magnitude. Current starts to flow in the coil, at box 706 of flowchart 700, slowly at first, because the back emf of the coil nearly cancels out the voltage across it. In FIG. 8, which schematically shows the current 800 in the coil as a function of time, shown on axis 802, and the voltage 804 across the capacitor as a function of time, the pulse is initiated at time 806. As the current in the coil starts to build up, the capacitor starts to discharge. At time 808, as stated in box 708 of flowchart 700, the capacitor has completely discharged, and almost all of its energy has gone into the electromagnetic field energy of the coil, which reaches a maximum current. The current, continuing in the same direction, starts to charge up the capacitor with the opposite polarity, as stated in box 710 of flowchart 700. At time 810, the capacitor has charged up to the operating voltage, but with polarity opposite to what it was at time 806, and the current and voltage across the coil has fallen to zero, as stated in box 712 of flowchart 700. The interval from time 806 to time 810 is one half of a wave period at the resonant frequency $(LC)^{-1/2}$ to first approximation, ignoring the effects of ohmic losses and any other dissipation. Again ignoring dissipation, the current as a function of time between times 806 and 810 is nearly a sine function, at the resonant frequency. The voltage across the capacitor as a function of time between times 806 and 810 is also nearly a sine function, but 90 degrees out of phase with the current as a function of time.

At time 810, if terminal 1408 remains at the negative operating voltage of terminal 1412, or if terminal 1408 is floated, indicated by "State 3" in FIG. 6, then no more current will flow in coil 1402, and capacitor 1404 will remain fully charged at the negative operating voltage, as stated in box 714 of flowchart 700. This state, between pulses, will persist until terminal 1408 is switched back to having the positive voltage of terminal 1410, shown in box 716 of flowchart 700 which is done at time 812 in FIG. 8. The capacitor will start to discharge again, and the current builds up again in the coil, as stated in box 718 of flowchart 700, but this time the current will be in the opposite direction from what it was between time 806 and time 810. The current after time 812 will have the same magnitude as a function of time, though opposite in sign, as it had between times 806 and 810, as the capacitor discharges, building up the electromagnetic field of the coil, and then charges up again with its original positive polarity, recovering field energy from the coil, as stated in boxes 720 and 722 of flowchart 700. At time 814816, as stated in box 724 of flowchart 700, half of a resonant frequency wave period after time 812, the capacitor will again be charged to the operating voltage, with its original positive polarity, and the coil current and voltage will again be zero. The circuit has now returned to its state before time 806, and can remain in this between-pulse state until a new current pulse is initiated by changing the voltage of terminal 1408. Optionally, terminal 1408 is floated until the next pulse is initiated.

The resonance frequency $(LC)^{-1/2}$, which is related to the pulse time as explained above, is optionally between 10 and 100 kHz. Alternatively it is between 1 and 5 kHz, or between 5 and 10 kHz, or between 100 and 200 kHz, or between 200 and 500 kHz, or between 500 kHz and 1 MHz, or more than 1 MHz.

Figure 13:
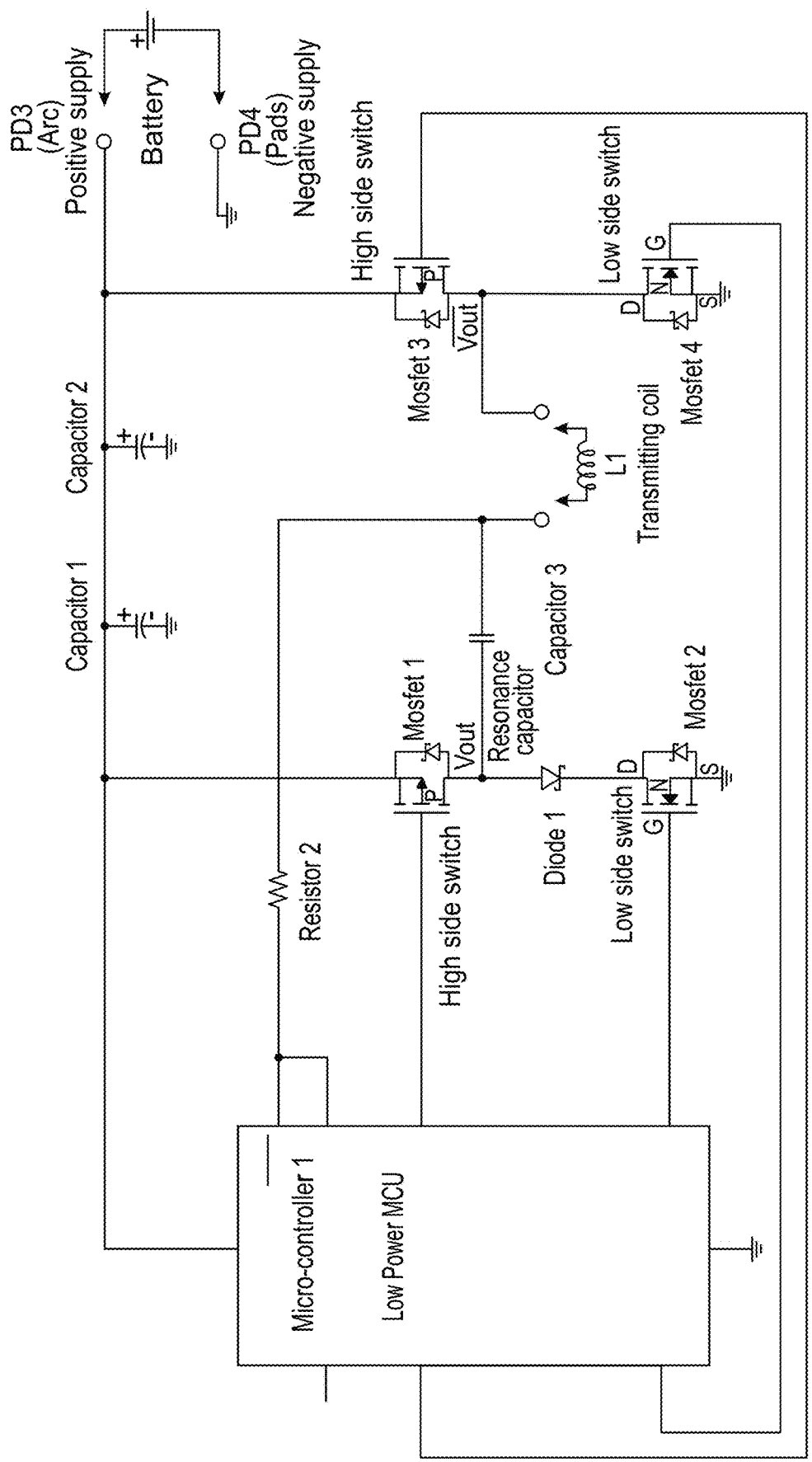
FIG. 13 is a circuit diagram for an energy-saving resonant circuit which could be used by the electronic patches of FIG. 1, FIG. 4A, FIG. 4B, or FIG. 4C to generate pulsed electromagnetic fields, according to an exemplary embodiment of the invention.

FIG. 13 is an exemplary circuit diagram for the energy saving circuit, showing how the principles of the circuit in FIG. 6 may be implemented. The switching of the voltage across the capacitor and coil in series between the positive and negative operating voltage is accomplished by switches based on FETs, which are opened and closed by applying an appropriate voltage to them. A microprocessor generates the signals, positive or negative square wave pulses that control the state of the FETs. Those signals are shown in FIG. 16, which also shows the current in the coil as a function of time. In FIG. 16, a pulse with positive current is always followed immediately by a pulse with negative current, so the capacitor always has the same sign of operating voltage, for example positive operating voltage, during the intervals between pulses. These back-to-back pulses together last for a whole cycle of the LC resonant frequency.

Use of Second Coil as a Position Sensor

Figure 9:
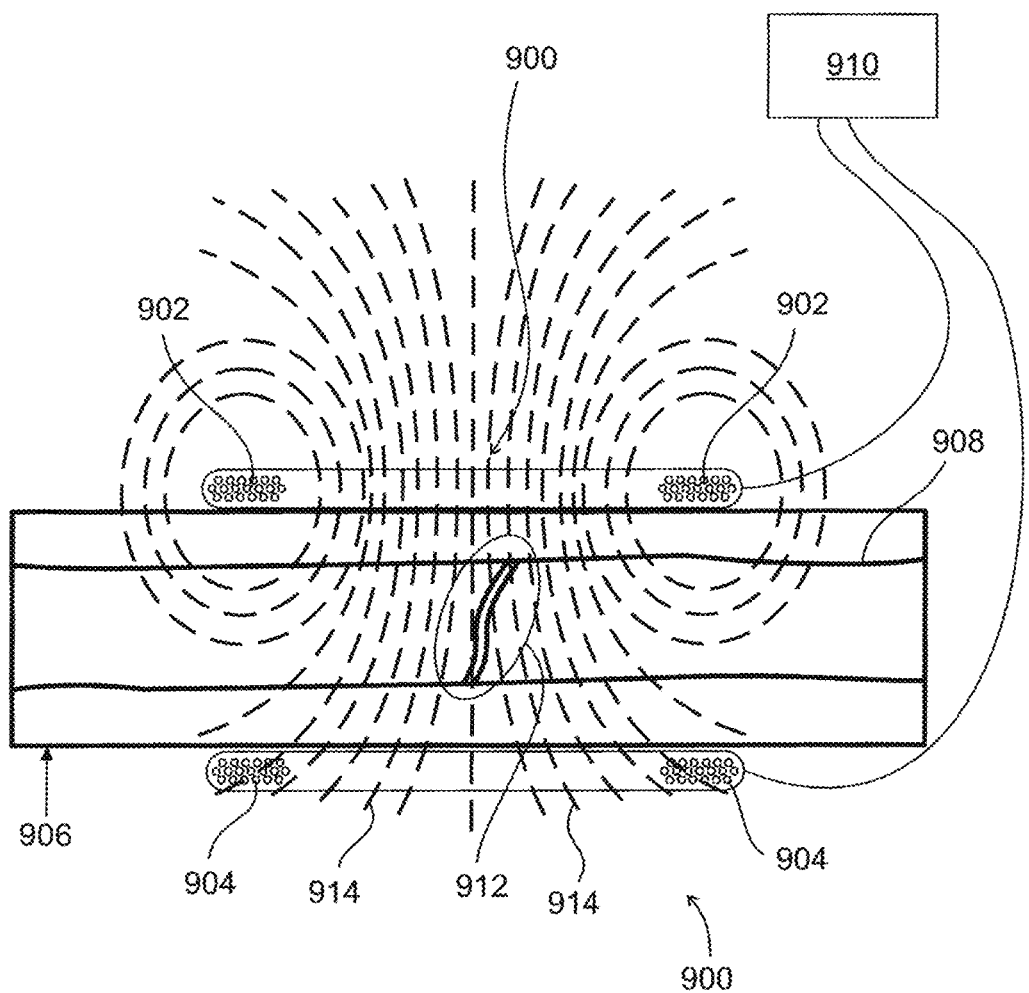
FIG. 9 is a schematic side view of a two-coil electronic patch wrapped around a cylindrical body part, such as a limb, in which changes in distance between the coils can be detected by using current in one coil to induce an emf voltage in the other coil, according to an exemplary embodiment of the invention.

FIG. 9 schematically shows an electronic patch 900 with two coils, in which one of the coils can be used as a sensor by measuring the emf induced in it by the other coil. Coil 902 is on top, and coil 904 is on the bottom, of a cylindrical body part 906, containing a bone 908. A controller 910 generates current pulses through coil 902, that create an electromagnetic field for treating a fracture site 912 in bone 908.

Controller 910 is optionally part of an electronics package incorporated in patch 900, similar to electronic package 7 in FIG. 1, or electronics package 410 in FIG. 4A, and controller 910 and patch 900 are optionally powered by a battery, similar to battery 9 in FIG. 1, or battery 408 in FIG. 4A. Alternatively, controller 910, and/or a power supply that powers it and/or patch 900, are not part of patch 900 at all, but may be larger units external to patch 900.

Some of the magnetic flux lines 914, generated by coil 902, also pass through coil 904. At the time shown, at least, coil 904 does not have any current passing through it, and does not generate its own electromagnetic field at the fracture site. But by measuring the emf voltage generated by the changing magnetic flux going through coil 904, controller 910 can obtain information that can be useful for calibrating and adjusting the field generated by patch 900.

Figure 10:
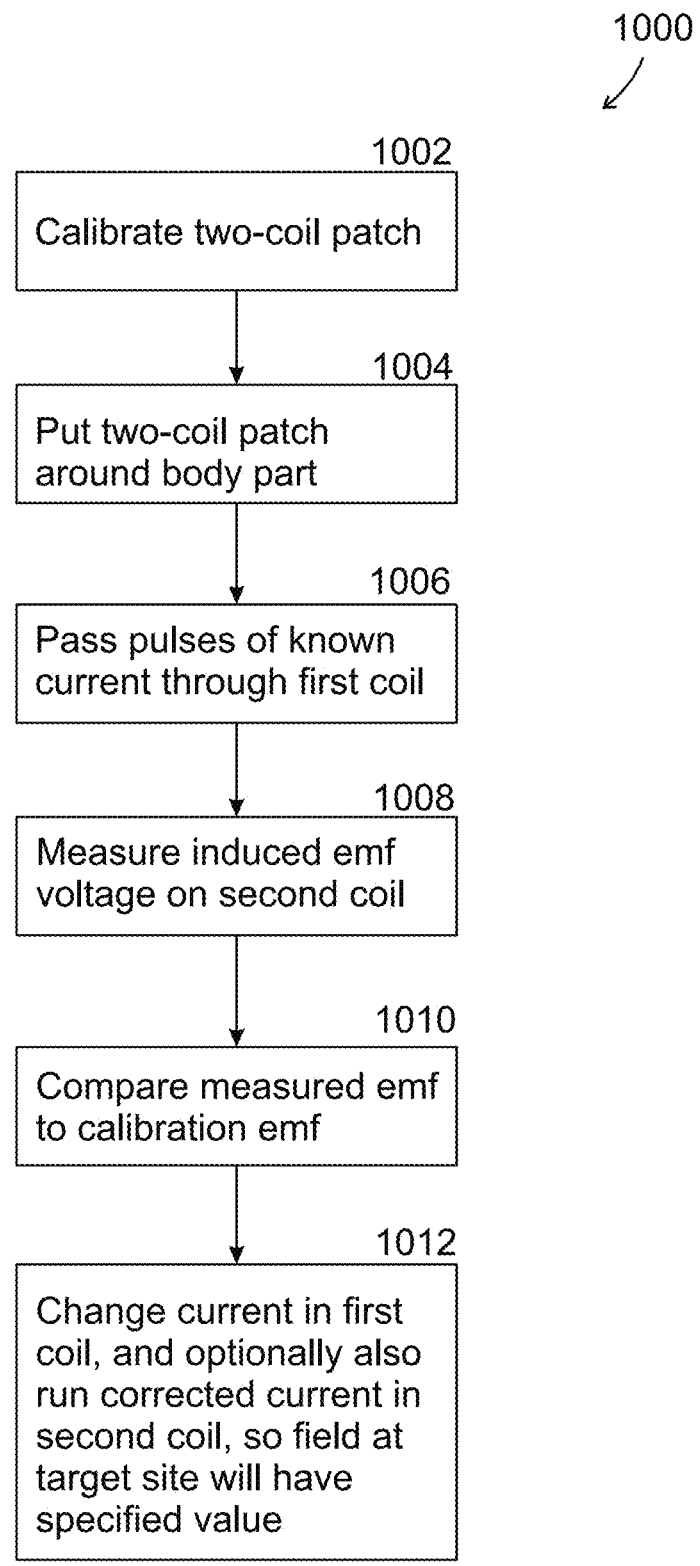
FIG. 10 is a flowchart showing how the electronic patch of FIG. 9 can be used to adjust the intensity of the electromagnetic field at a target site to a specified value, according to an exemplary embodiment of the invention.

FIG. 10 shows a flowchart 1000 illustrating an exemplary manner in which patch 900 operates. At 1002, the patch is calibrated. This is done by measuring the emf in coil 904, when a known current, with known pulse shape and width, is passed through coil 902, with coil 904 at a known position and orientation with respect to coil 902. For example, coils 902 and 904 are held with their axes aligned, separated by a known distance. For example, the known distance is a standard distance that the coils would be separated, for a cylindrical body part, optionally a specific body part that the patch is designed to treat, such as a forearm at the wrist, of a standard size. Optionally, the current passed through coil 902 is the current needed in order to produce a specified electromagnetic field strength, for example a field strength that is believed to work well for therapy, with that pulse shape and width, at a standard target location in the body part. Once patch 900 has been calibrated, it is possible to calculate what current should be passed through coil 902, for that pulse shape and width, in order to produce the specified electromagnetic field strength at a given location relative to coil 902. At 1004, patch 900 is placed around a cylindrical body part, such as body part 906.

At 1006, a known current, of known pulse shape, optionally the same current and pulse shape used in calibrating patch 900, is passed though coil 902, and at 1008, the emf in coil 904, induced by the current in coil 902, is measured. By comparing the measured emf, to the measured emf found during the calibration, at 1010, it is possible to estimate what electromagnetic field strength would be produced at the target location by that current in coil 902, and to estimate how the current in coil 902 should be changed to produce the specified therapeutic electromagnetic field strength at the target location. At 1012, the current in coil 902 is changed to that estimated value, and therapy is performed using the adjusted value of the current.

Optionally, patch 900 also has a mode of operation where coil 904 generates its own therapeutic electromagnetic fields at the target location in body part 906 that add to the fields generated by coil 902. In this case, coil 904 also has current going through it, when treatment is performed, and the current going through coil 904 is taken into account, in calculating the current that should be passed through coil 902, in order to obtain the specified electromagnetic field strength at the target location. Optionally, the emf measured in coil 904 is also used to adjust the current going through coil 904, in order to produce a specified therapeutic electromagnetic field strength at the target location.

When patch 900 has a mode of operation where coils 902 and 904 are both used to generate fields at the target location in the body part, it optionally stays in this mode of operation most of the time, while treatment is continuing. But occasionally, or at regular intervals, patch 900 may go into the mode of operation where coil 904 is used to measure the emf induced by coil 902, at least for a short time. This may be done, for example, if medical personnel request a reading on emf in coil 904, for example using a communications link with controller 910. Alternatively or additionally, controller 910 may be programmed to switch patch 900 to the mode where emf is measured in coil 904, for a short time, for example for 1 second, at regular intervals, for example once an hour, or once a day. Optionally, the regular measurements of emf in coil 904 are used in a closed feedback loop to keep the electromagnetic field strength at the target location at a specified value.

Optionally, the emf measured in coil 904 is used to calculate the distance between coil 902 and coil 904, when patch 900 is in place around body part 906, and that distance is used to estimate the distance from coils 902 and 904 to the target location, and then to estimate how much current is needed in coils 902 and 904 to produce the specified electromagnetic field strength at the target location, for example using magnetic simulation software. Alternatively, the distance from coil 902 to coil 904, and the distance to the target location, is never calculated explicitly, but the measured emf of coil 904 when patch 900 is in place around body part 906 is compared to the measured value of emf when patch 900 was calibrated, for example a ratio and/or difference in the emf values is found, and that ratio and/or difference is used directly to calculate the current that should be used in coils 902 and 904 to obtain the specified electromagnetic field strength at the target location.

The measured emf of coil 904, and/or the distance between coil 902 and coil 904 that can be calculated from it, may also be used in other ways, to obtain information about the state of body part 906. For example, the emf of coil 904, induced by coil 902, is regularly measured during the course of treatment of body part 906. If the distance appears to be increasing over time, because the measured emf in coil 904 is decreasing over time, for the same current in coil 902, then that might indicate that body part 906 is undergoing swelling. Optionally, the measurements of emf of coil 904 are communicated to medical personnel, using a communications channel, for example a wireless communications channel, in controller 910. Based on the degree and rate of swelling inferred from the emf measurements, the medical personnel might decide that some medical intervention is appropriate, to reduce the swelling. Alternatively, the medical personnel might decide, on the basis of the emf measurements, that the swelling is of a degree expected for that kind of bone fracture, and that no intervention is necessary.

If the distance between coil 902 and 904 is inferred to be decreasing over time, from an increase in the induced emf in coil 904 for a given current in coil 902, then that might indicate that body part 906 is shrinking, perhaps due to a reduction in swelling as the bone fracture heals, or due to wasting of muscle. Whatever the cause of the shrinkage of body part 906, it might indicate that the cast is becoming too loose, and can no longer keep bone 908 in place while the fracture is healing. In that case, it might be medically advisable to remove the cast and to replace it. On the other hand, if body part 906 is shrinking, but more slowly than expected, that might indicate that bone 908 is failing to heal properly.

Exemplary Use of Patch Under a Cast

Figure 11:
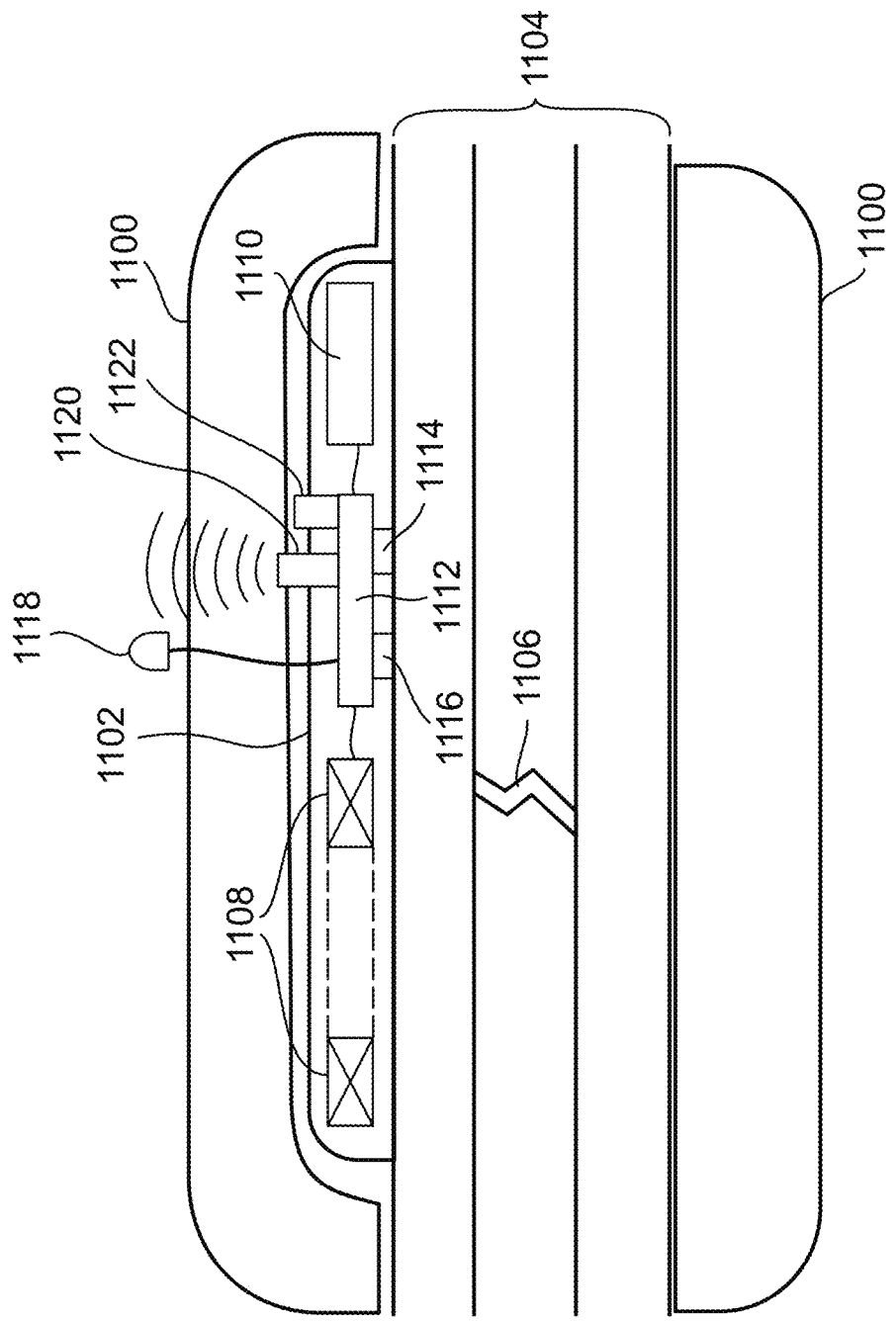
FIG. 11 is a schematic side view of an electronic patch, similar to the patch of FIG. 1 or FIG. 4A-4C, in place on a body part with a fractured bone site, under a cast, showing a wireless communications link and various sensors and a device for activating and deactivating the electronic patch, according to an exemplary embodiment of the invention.

FIG. 11 schematically shows a cast 1100 covering an electronic patch 1102, in contact with body part 1104, within which there is a fracture site 1106 that is being treated by electromagnetic fields generated by electronic patch 1102. Electronic patch 1102 includes a coil 1108, a battery 1110, and an electronics package 1112. Optionally, there is also a second coil, as described for example for the patch shown in FIG. 4A or FIG. 4B. Optionally, electronic patch 1102 includes sensors that can obtain data directly from the skin of the body part, under the cast. For example, sensor 1114 is a pressure sensor, and sensor 1116 is a blood oxygen sensor. The sensors are optionally part of electronics package 1112, or at least are connected to the electronics package for power and data processing. Optionally, one or more of the sensors causes a warning light 1118, located outside the cast, to light up under certain conditions, such as low blood oxygen level which can indicate that the cast is too tight. Both the pressure sensor and the blood oxygen sensor can be used to detect if the pressure under the cast is rising, for example due to swelling of body part 1104, or if the pressure is too high because the cast was placed too tightly to begin with, which can interfere with blood circulation, causing a drop in blood oxygen levels in the skin under the cast. The pressure sensor can also detect when the pressure under the cast is falling, which might mean that swelling of the body part is decreasing, or muscle mass is being lost. If the pressure decreases too much, the cast might be too loose to effectively hold the fractured bone in place, and it might be medically advisable to remove the cast and replace it with a cast that fits better.

Communications link 1120, optionally a wireless communications link, is optionally used to transmit the sensor data, and other data generated by patch 1102, to medical personnel, including data on the emf induced in a second coil, as described above in FIGS. 9 and 10. Communications link 1120 is optionally one-way, for example communicating data from patch 1102 to medical personnel. Alternatively, communications link 1120 is two-way, and is used by medical personnel to control the operation of patch 1102 when it is under cast 1100, and is not easily accessible. For example, medical personnel could use communications link 1120 to request patch 1102 to obtain certain data, or to turn patch 1102 on or off, or to change parameters of its operation, such as the pulse repetition rate or the field amplitude. Alternatively, communications link is one-way, but is used only to control patch 1102 from the outside, not to obtain data from it.

Optionally patch 1102 has an on/off switch 1122. Optionally, switch 1122 is used only before patch 1102 is covered by cast 1100, and cannot be accessed once patch 1102 has been covered. Alternatively, switch 1122 can be used when patch 1102 is covered by cast 1100. Possible designs for switch 1122 include:
1. A capsule that, when broken, turns the patch on, for example like a light stick.
2. An external activator that turns on the patch remotely using electromagnetic induction.
3. A pull wire.
4. A magnetic switch turned on and off by a magnet.

Optionally switches operating by any of these methods, or any other method, can also be used to initiate a test to see if the patch is operating properly, and can be used to change settings such as power levels.

Optionally, if the battery is rechargeable, it can be recharged using coil 1108, or another coil not shown in FIG. 11, by using an external coil to transfer power to coil 1108 inductively, even if coil 1108 is below the cast.

FIGS. 14 and 15 show block diagrams for circuitry that allows the coil to receive an external command to activate the patch when it is de-activated. In FIG. 14, the coil, labeled "Field transmission coil" functions as a radio receiver coil, receiving a signal from an external activator, to activate the patch. The coil passes the signal to an Incoming RF Command Detector, which interprets the signal, and tells the Master ON/OFF control to activate the energy saving circuit that generates the pulses. There is also a "Switch Control timer ON/OFF timing" module shown in FIG. 14, which connects or disconnects the energy saving circuit and the battery, using the High Speed Switch, according to the on and off times set in the timer. FIG. 15 provides more details of how the block diagram of FIG. 14 is implemented in a system designed by the inventors. The Rx buffer module in FIG. 15, similar to the Incoming RF Command Detector in FIG. 14, interprets RF signals transmitted by an external activator and received by the field transmission coil, and sends the ON/OFF commands to a Micro-controller. The Micro-controller, which is always connected to the battery in order to receive the ON/OFF commands, connects or disconnects the battery from the Tx Driver, the circuitry, shown schematically in FIG. 6 and in more detail in FIG. 13, that generates the pulses of current. The Tx Driver is shown connected to the resonance capacitor and the field transmission coil in series, as shown in FIG. 6. Optionally, the field transmission coil is still capable of receiving commands from the activator, even when the coil is generating current pulses, because the RF signals are at a much higher frequency than the current pulses, and can be separated from the current pulses by an appropriate filter.

Figure 12:
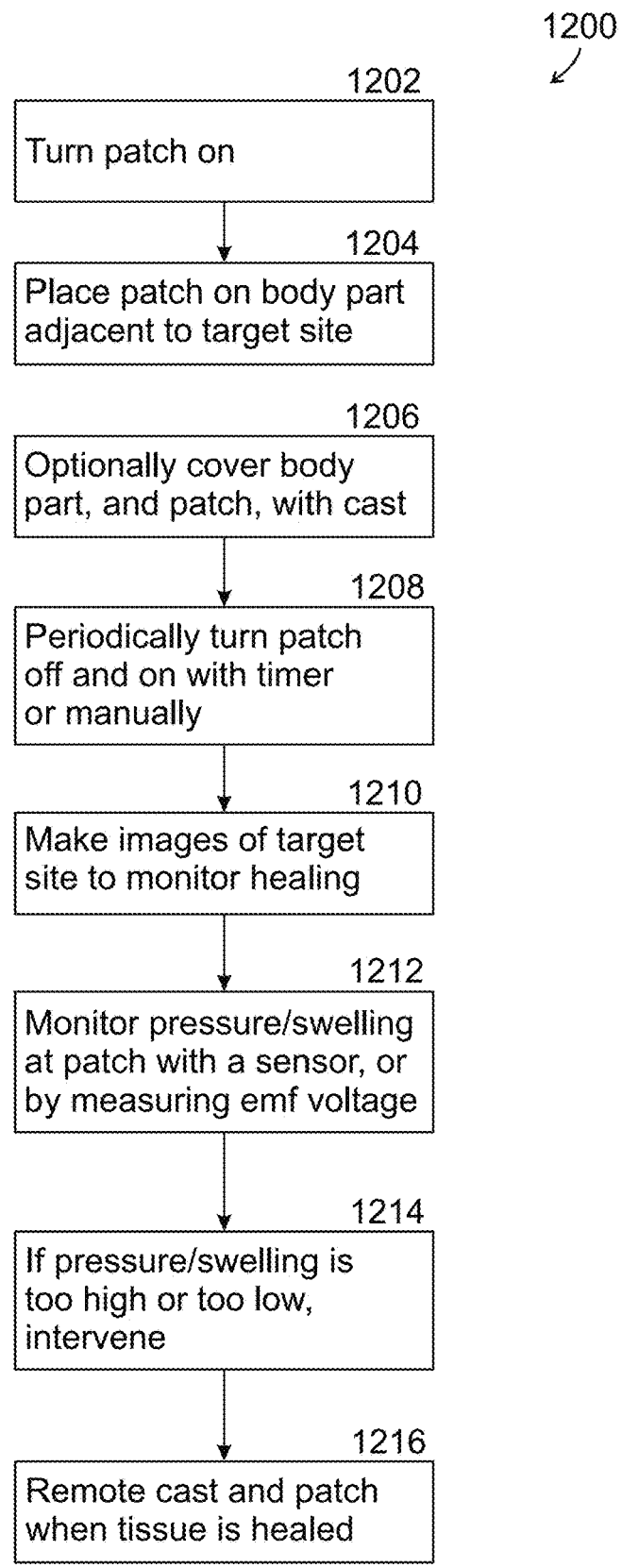
FIG. 12 is a flowchart for events that occur in the use of an electronic patch, such as those shown in FIG. 1 and FIGS. 4A-4C, for treatment of tissue.

FIG. 12 shows a flowchart 1200, for events that occur during the time an electronic patch, such as those described herein, is used to promote tissue healing at a target site, such as a fractured bone site, using pulsed electromagnetic fields. Flowchart 1200 is primarily concerned with an electronic patch that is located under a cast, but is not limited to that case.

At 1202, the patch is turned on. At 1204, the patch is placed on a body part adjacent to the target site. At 1206 the body part, optionally including the patch, is optionally covered with a cast. At 1208, during the course of treatment, the patch is periodically turned off and on. For example, the patch is optionally turned on for only a limited number of hours each day. Turning the patch off and on is optionally done automatically with some kind of timer, possibly a timer function in the electronics package, such as the "Switch Control Timer" module shown in FIG. 14. Alternatively, it is done manually, for example using a switch that is accessible outside the cast, if there is a cast covering the patch. For example, an external activator is optionally used to turn on the patch when it is "sleeping" by sending a radio signal that is received by the coil, interpreted by the Incoming RF Command Decoder module shown in FIG. 14, and sent to the Master ON/OFF control module. Of course, the Switch Control Timer module, the Master ON/OFF control module, and the RF Command Decoder module are all optionally powered on, connected to the battery, even when the patch is deactivated, so that these modules can operate as described, to turn the patch on.

At 1210 medical images are optionally made of the body part, to monitor the tissue healing, for example x-ray images. At 1212, pressure and/or swelling of the body part is optionally monitored, using a sensor under the cast, or using a second coil to measure emf voltage induced by a first coil. At 1214, if the pressure and/or swelling is found to be too high or too low, some kind of intervention is optionally taken. At 1216, the cast and the patch are removed at the end of treatment, for example when the tissue is healed.

Parameters for Different Bones

Table 1 shows exemplary coil parameters that the inventors believe will be useful for several different types of bones.

TABLE 1

Parameters of coils for different bones

| Type of bone | Dimensions of patch (cm) | Distance from patch to target site (cm) | Max. patch thickness (mm) | Number of coils | Other features |
| --- | --- | --- | --- | --- | --- |
| Arm | 12 to 20 by 8 to 12 | 1.5 to 2.5 | 5 | 2 | Measure emf |
| Leg | 32 to 50 by 16 to 25 | 5 to 8 | 5 | 2 | Measure emf |
| Pelvis | 32 to 50 by 12 to 20 | 5 to 8 | 5 | 2 | Measure emf |
| Sternum | 8 to 12 by 8 to 12 | 0.5 to 4 | 10 | 1 | Different power settings |
| Ribs | 4 to 6 by 8 to 12 | 0.5 to 4 | 10 | 1 | Different power settings |
| Skull | 6 to 10 by 6 to 10 | 0.3 to 2 | 10 | 1 | |
| Spine | 4 to 6 by 6 to 10 | 0.3 to 2 | 10 | 1 or more | Different power settings |

Different power settings are optionally used for different individuals who have different amounts of subcutaneous fat in their bodies, which can affect the distance from the coil to the target site in the bone, and hence the power needed to produce electromagnetic fields of a specified intensity at the target site. For example, there may be different power settings for thin men, overweight men, thin women, and overweight women. The goal may be to produce a magnetic field of between 50 and 500 µT at the target site, for example 200 µT.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find calculated support in the following examples.

EXAMPLES

Reference is now made to the following examples, which together with the above descriptions illustrate some embodiments of the invention in a non limiting fashion.

It is an object of the present invention to provide means to promote bone fixation or fusion in a significantly reduced recovery time relative to prior art means.

The present invention, in some of its embodiments, provides an electronic patch for stimulating osteogenesis at a fractured bone site, comprising a continuous coil (or coils), a power source, a controller with a power saving circuit, also referred to as an energy saving circuit, which is connected to a conductor of said coil and is powered by said power source in order to control properties of a generated electromagnetic field that propagates from said coil to a fractured bone site, wherein said coil, power source and controller are integrated with a flexible substrate externally applied to an injured limb associated with said fractured bone site.

In one aspect, the coil is of symmetric configuration, and the coil is configured to cause electromagnetic fields propagating from corresponding portions thereof to become superposed one with the other at the fractured bone site and to increase stimulation of osteogenesis there at.

In one aspect, the controller comprises a pulsed current modulator. Each pulse that is generated by the current modulator is of a sufficient duration to ensure that the total accumulated amount of energy associated with the electromagnetic field that is absorbed during a predetermined period by a bone region associated with the fractured bone site is greater than a predetermined amount.

In one aspect, a timer is adapted to modulate a pulsed waveform in continuous ongoing fashion according to a desired duty cycle. It should be understood that "duty cycle" here may have a different meaning than it has in some of the description above, where it refers to the fraction of pulse time within the pulsed waveform. Here, it may refer to the fraction of time that the pulsed waveform is being produced.

In one aspect, the timer is adapted to modulate a pulsed waveform and propagation direction, for a predetermined modulation duration, in order to save battery power consumption using a pendulum like effect.

In one aspect, the generated electromagnetic field has a flux density ranging from 0.1 to 0.5 mT, 0.5 to 0.8 mT, 0.8 to 2 mT, 2 to 5 mT, or 0.2 to 5 mT at the point of fracture.

In one aspect, the frequency of the pulsed current ranges from 1 to 1000 Hz, 1 to 100 kHz, or 1 Hz to 100 kHz and 100 KHz to 40 MHz.

In one aspect, the pulsed current has an average amplitude ranging from 10 nA to 50 µA, 15 to 100 µA, 0.1 to 2 mA, 20 to 3000 mA, or 1 µA to 2000 µA.

In one aspect, the control module may be comprised of a circuit wherein a ratio between said maintaining and said charging ranges from about 1:600 to about 1:5000.

In one aspect, the pulsed current has a pulse duration ranging from 5 to 30 microseconds, 30 to 50 microseconds, 50 to 200 microseconds, or 5 to 200 microseconds.

In one aspect, the pulsed current has a pulse duration ranging from 1.3 milliseconds to 67 milliseconds.

In one aspect, the timer is adapted to modulate a pulsed waveform selected from the group consisting of a square waveform, a triangular waveform, a sawtooth shaped waveform, and a sinusoidal waveform.

In one aspect, the coil has a number of turns ranging from one to ten.

In one aspect, the coil has a number of turns ranging from one to 1000.

In one aspect, the coil has a number of turns ranging from 300 to 1000.

In one aspect, the coil has a number of turns ranging from 15 to 300.

In one aspect, the power source is a battery that has a sufficient capacity for powering the current modulator during an entire anticipated healing period.

In one aspect, the power source is selected from the group consisting of a piezoelectric device for generating piezoelectricity, a capacitor, a dynamo, and an electro-kinetic actuator.

The electronic patch may be disposable, adapted for one-time use, or reused and may be applied below or above a cast.

The electronic patch may have a circular configuration, a rectangular configuration, and the radial spacing between each pair of adjacent turns may be different.

The electronic patch may comprise a controller for controlling the properties of the generated electromagnetic field. The controller may comprise one or more of the following:
  a current modulator;
  a power saving circuit;
  a timer;
  a microswitch;
  an oscillator;
  a wireless transceiver;
  an inverter.

The electronic patch may include electronic components that are manufactured by thinned die thermocompression laminated into LCP films.

The printed electronics techniques may include a rigid PCB and battery with an appropriate spacing between them to provide a level of flexibility.

The electronic patch may include an oscillator that is adapted to generate current pulses which are rectangular, triangular, sawtooth, and sinusoidal waveform.

A timer may be used to modulate the waveform by periodically deactivating the power supply from the battery to the oscillator in order to achieve a desired duty cycle which is essential for saving energy.

The electronic patch may further comprise an inverter in electrical communication with the oscillator for periodically changing the direction of the magnetic field lines and to thereby additionally improving the rate of osteogenesis.

The controller may be adapted to operate in a sleep mode whereby the electronic components are inactive when the electronic patch is in storage.

In one aspect, the following combination of parameters are used:
  a) a patch thickness of 2-10 mm;
  b) a patch diameter of 50-100 mm;
  c) a battery capacity of 300-800 mA*hr, or 90-2000 mA*hr, or 30-2000 mA*hr;
  d) a nominal battery voltage of 3-10 V, or 3-20 V;
  e) a maximum battery current of 2 A;
  f) a maximum pulse current of 1.5 A, or 3 A;
  g) an electromagnetic field frequency of 50-500 kHz or 10-100 kHz;
  h) 2-50 pulses per second;
  i) a duty cycle of 1:750-1:5000;
  j) a flexible substrate made of biocompatible silicone;
  k) wireless activation;
  l) Field strength: 0.1 to 0.5 mT
  m) Coil current: 50 mA to 2 A or 6 A (p-p)
  n) Pulse duration: 10 us to 100 us
  o) Pulse shape: sinusoidal An aspect of the present invention, in some of its embodiments, is an electronic patch applied externally to an injured limb, particularly one associated with a fractured bone. In certain circumstances, a physician monitoring recovery of the fractured bone may decide to apply the electronic patch below or above a cast. The electronic patch comprises a constantly operable current modulator for generating an electromagnetic field that effectively stimulates osteogenesis, or bone development. Even though the patch comprises electronic components, it is sufficiently flexible in order to be applied around the circumference of the injured limb. The electronic patch may be disposable, adapted for one-time use, or alternatively may be reused.

Patch 10 in FIG. 1 comprises a continuous coil 5, which may be a multi-turn coil or coils, for focusing the generated electromagnetic field onto a fractured bone site. Coil 5 is shown in FIG. 1 as a circular configuration where the radial spacing between each pair of adjacent turns is uniform, but it may also be of any other symmetric configuration, such as rectangular, or any asymmetric configuration, and the radial spacing between each pair of adjacent turns may be different. When patch 10 is positioned on top of a flat surface, all turns of coil 5 are coplanar, and each turn is concentric with an adjacent turn.

A controller, part of electronics package 7, powered by battery 9 is connected to the conductor of coil 5 in order to control the properties of the generated electromagnetic field that propagates from the coil to the fractured bone site. The controller comprises a current modulator and a power saving circuit for regulating the current needed to generate the electromagnetic field, but may also comprise other electronic components selected from, but not limited to, a timer, microswitch, oscillator, wireless transceiver, and inverter.

Although the only two illustrated components that are shown to be positioned radially inwardly relative to coil 5 are electronics package 7 and battery 9, it will be appreciated that any other electronic component may be positioned externally to electronics package 7 insofar as it retains the compactness of patch 10 by being positioned radially inwardly relative to coil 5.

As described above, patch 10 may be imparted with sufficient flexibility to facilitate application thereof around the circumference of an injured limb. To achieve the required degree of flexibility, the electronic components may be manufactured by low-cost printed electronics techniques and embedded within, or otherwise integrated with, one or more flexible substrates 3 to produce a monolithic patch. Each flexible substrate 3 may be a silicone substrate, a polyimide substrate, a liquid crystal polymer (LCP) substrate, a multi-layer film laminate substrate, a foil substrate, or a combination thereof. Flexible electronic components may be fabricated by thinned die thermocompression laminated into LCP films such that the films completely encapsulate the die.

Alternatively, the printed electronics techniques may include a rigid PCB and battery with an appropriate spacing between them to provide some level of flexibility.

The bottom surface 11 of the flexible substrate 3 may be provided with application means, such as adhesive elements for adhesion to a skin surface or clips for engagement with a beard or other hair covered skin surface.

In order to minimize battery consumption, the oscillator is adapted to generate a plurality of current pulses, e.g. rectangular pulses, for exciting the coil by a desired frequency and magnitude, so as to induce a desired magnetic flux. Of course, other waveforms, such as a triangular, sawtooth, and sinusoidal waveform, may also be used to excite the coil. The timer modulates the waveform by periodically deactivating the power supply from the battery to the oscillator in order to achieve a desired duty cycle which is potentially useful for saving energy. An inverter in electrical communication with the oscillator may be employed in order to periodically change the direction of the magnetic field lines and to thereby additionally improving the rate of osteogenesis.

Also, the controller may operate in a sleep mode whereby the electronic components are inactive when the electronic patch is in storage. The controller becomes activated in response to a predetermined pressure sensed by the microswitch through the flexible substrate upon external application of the electronic patch to the injured limb. Alternatively, the controller may become activated by a wireless command transmitted to the transceiver, a pull trigger, a magnetic trigger or by applying an external electric induction.

As additional means to minimize battery consumption, the controller in conjunction with the timer may be operable to reduce the magnitude of the excitation current after a predetermined interval, e.g. a week, following activation of the controller. During this interval, the generated electromagnetic field stimulated osteogenesis at the fractured bone site to such a significant degree that the osteogenesis will continue even after the magnitude of the excitation current is reduced.

In addition to a battery, the electronic components may be powered by any other power source well known to those skilled in the art, including a piezoelectric device for generating piezoelectricity, a capacitor which is charged by a radiofrequency device located at the home of a patient and therefore would not require outpatient services, a dynamo, and an electro-kinetic actuator, for example one which employs a magnetic element that is displaceable along a coil.

FIG. 3 is a schematic cross sectional view of injured limb 15 to which electronic patch 10 is externally applied, illustrating the ability of the coil to focus the generated electromagnetic field onto fractured bone site 14. During operation of the current modulator, current flows through diametrically opposite coil portions on the left and right sides, and electromagnetic fields 17 on the left and right sides, respectively, propagate at a right angle to a corresponding conductor of a coil portion. The magnitude of the magnetic flux is greatest at the skin surface at the top of limb 15, and is reduced as a function of the distance from the conductor. At a predetermined depth below the skin, surface coinciding with the location of fractured bone site 14, e.g. 30 mm, electromagnetic fields 17 from the left and right coil portions become superposed one with the other. Even though the magnitude of the magnetic flux has become reduced at fractured bone site 14, it is additive with respect to the electromagnetic field propagating from the diametrically opposite coil portion. Similarly, other electromagnetic fields propagating from other corresponding coil portions become superposed one with the other at fractured bone site 14. Fractured bone site 14 accordingly becomes impinged by an electromagnetic field having a surprisingly high magnitude of magnetic flux that accelerates stimulation of osteogenesis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An electronic patch for stimulating tissue healing at a target site, comprising:
    a) a battery or an arrangement of multiple batteries less than 5 mm thick;
    b) a capacitor connected directly to a coil in series;
    c) pulse generating circuitry, powered by the battery or batteries, which applies a voltage across the capacitor and coil in series, and repeatedly changes the voltage across the capacitor and coil in series, to produce pulses of current in the coil, the current producing an electromagnetic field at the target site for stimulating tissue healing, wherein more than 50% of the electromagnetic field energy of a pulse is transferred into electrostatic energy of the capacitor and converted back into electromagnetic field energy of a next pulse;
wherein the patch is flexible enough to generally conform to an external body surface adjacent to the target site, and wherein the pulse generating circuitry repeatedly changes the voltage by alternating between applying a voltage across the capacitor and coil in series for a duration of one pulse, and applying a different voltage across the capacitor and coil in series for a duration of a following pulse, producing consecutive pulses of about the same duration and with currents in opposite directions, and wherein the pulse generating circuitry is configured in a manner that, during the duration of one pulse upon a voltage being applied across the capacitor and coil in series, the capacitor completely discharges and charges up with an opposite polarity, before the different voltage is applied across the capacitor and coil in series.

2. The electronic patch according to claim 1, wherein the durations of the pulses are about equal to half a wave period of an $(LC)^{-1/2}$ resonance frequency of the coil and capacitor, to lowest order in a fraction of the electromagnetic field energy that is dissipated during each pulse, where L is an inductance of the coil and C is a capacitance of the capacitor.

3. The electronic patch according to claim 1, wherein the pulse generator is configured to produce one or more further pulses during which the coil produces the electromagnetic field at the target site, with at least some of the pulses alternating with non-pulse periods in which the current in the coil is less than 3 µA.

4. The electronic patch according to claim 3, wherein the pulse generator is configured to produce pulses at intervals in a manner that a duty cycle, defined as a ratio of durations of the pulses to the total time, is less than 1%.

5. The electronic patch according to claim 3, wherein the non-pulse periods are between 0.02 and 0.5 seconds.

6. The electronic patch according to claim 1, wherein more than 90% of the electromagnetic field energy of a pulse is transferred into electrostatic energy of the capacitor and back into electromagnetic field energy of a next pulse.

7. The electronic patch according to claim 1, wherein any rigid component of the patch is no wider than 25 mm in a direction that the patch is flexible in, and any two rigid components of the patch, arranged in a direction that the patch is flexible in, are separated by at least 1.5 mm.

8. The electronic patch according to claim 1, configured to produce current pulses that consume less than 2000 mA-hrs of battery current with the electronic patch running for 50 days.

9. The electronic patch according to claim 1, less than 10 mm thick including the battery or batteries, the capacitor, the coil, and the pulse generating circuitry.

10. The electronic patch according to claim 1, wherein a duration of each pulse is between 5 microseconds and 100 microseconds, in steady state operation.

11. The electronic patch according to claim 1, wherein the peak current in the coil is between 25 mA and 3 A.

12. The electronic patch according to claim 1, wherein the magnetic field at the target site is between 0.05 and 0.5 mT.

13. The electronic patch according to claim 1, wherein the patch comprises a substrate of a flexible bio-compatible material, which provides the patch with flexibility.

14. The electronic patch according to claim 1 that is water resistant for two half-hour exposures to water each day for 50 days.

15. A method of treating a fractured bone site in a body part, comprising:
 a) applying the electronic patch of claim 1 to an outer surface of the body part;
 b) setting the body part in a cast that covers the electronic patch; and
 c) while the electronic patch is covered by the cast, using the controller to produce an electromagnetic field at the fractured bone site suitable for stimulating tissue healing, during multiple pulses, with more than 50% of the electromagnetic field energy being transferred into electrostatic energy of the capacitor and back into electromagnetic field energy of a next pulse.

16. The method according to claim 15, wherein the electronic patch comprises a pressure sensor with a communications link to the outside of the cast, the method also comprising measuring a pressure of the cast against the body part, or the electronic patch comprises a blood oxygen sensor with a communications link to the outside of the cast, the method also comprising measuring a blood oxygen level in skin of the body part, or the electronic patch comprises both the pressure sensor and the blood oxygen sensor and the method also comprises measuring both the pressure of the cast and the blood oxygen level in the skin, at different times during the treatment of the bone site and communicating the measurement results over the communications link.

17. The electronic patch according to claim 1, also comprising:
 a) a pressure sensor configured to measure a pressure of a cast worn by the patient over the electronic patch, or a blood oxygen sensor configured to measure a level of blood oxygen in skin of the patient adjacent to the electronic patch, or both; and
 b) a communications link configured to communicate results of the sensor measurement or measurements.

18. The electronic patch according to claim 1, for use on a cylindrical body part, sized to wrap at least part way around the cylindrical body part, with a first portion of the patch, comprising the coil, on one side, and a second portion of the patch comprising another coil, on another side, with the another coil also contributing to the electromagnetic field at the bone site while current flows in the another coil, and with the pulse generator configured to transfer more than 50% of the electromagnetic field energy of both coils for a pulse into electrostatic energy of the same and/or a different capacitor and back into electromagnetic field energy of both coils at a next pulse.

19. The electronic patch according to claim 1, for producing a specified level of the electromagnetic field at a target site in a cylindrical body part, the electronic patch comprising a first portion and a second portion, and configured for placing the first portion on one side and the second portion on a different side of the cylindrical body part, the first portion comprising the coil, and the second portion comprising a second coil also configured to contribute to the electromagnetic field at the target site while pulses of current run through the second coil, the electronic patch also comprising a controller configured to:
 a) measure an electromotive force (emf) voltage induced in the second coil based on the pulse generating circuitry generating pulses of current in the coil of the first portion;
 b) use the measured emf voltage to estimate a required level of current for the coil in the first portion, or to estimate required levels of current for the coil in the first portion and for the second coil, to produce the specified level of the electromagnetic field at the target site; and
 c) pass the required level of current for the coil in the first portion through that coil, or pass the required levels of current for the coil in the first portion and for the second coil through the coil in the first portion and through the second coil respectively, producing the specified level of electromagnetic field at the target site.

20. The electronic patch according to claim 1, for producing a specified level of the electromagnetic field at a target site in a cylindrical body part, the electronic patch comprising a first portion and a second portion, and configured for placing the first portion on one side and the second portion on a different side of the cylindrical body part, the first portion comprising the coil, and the second portion comprising a second coil also configured to contribute to the electromagnetic field at the target site while pulses of current run through the second coil, the electronic patch also comprising a controller configured to:
 a) measure an emf voltage induced in the second coil as the pulse generating circuitry generates pulses of current in the coil of the first portion;
 b) repeat (a) at one or more different times during a course of tissue healing;
 c) notify medical personnel once the emf voltage induced in the second coil by the current pulses increases or decreases over time at a rate that indicates a medically significant swelling or shrinking of the cylindrical body part.

21. The electronic patch according to claim 1, comprising a first part with the battery or an arrangement of multiple batteries, the capacitor connected directly with the coil in series, and the pulse generating circuitry, and a second part with a second battery or arrangement of multiple batteries, a second capacitor connected directly with a second coil in series, and a second pulse generating circuitry powered by the second battery or batteries, which applies a voltage across the second capacitor and second coil in series, and repeatedly changes the voltage across the second capacitor and second coil in series, to produce pulses of current in the second coil, said current also contributing to the electromagnetic field at the target site for stimulating tissue healing during the pulses, most of the electromagnetic field energy of the second coil being converted into electrostatic energy of the second capacitor and converted back into electromagnetic field energy of the second coil at a next pulse.

22. The electronic patch according to claim 1, adapted for stimulating tissue healing at a target site inside an injured limb, sized and sufficiently flexible to be applied around the circumference of the limb.

23. The electronic patch according to claim 1, wherein the coil has a radius greater than 30 mm, or the electronic patch has a diameter between 50 mm and 100 mm, or both.

* * * * *